US012569675B2

(12) United States Patent
Romot et al.

(10) Patent No.: US 12,569,675 B2
(45) Date of Patent: Mar. 10, 2026

(54) ELECTRODE APPARATUS FOR TISSUE STIMULATION AND RELATED METHOD OF USE

(71) Applicant: Axogen Corporation, Alachua, FL (US)

(72) Inventors: Brian Romot, Alachua, FL (US); Justin Deuerling, Alachua, FL (US); Curt Deister, Alachua, FL (US); Angelo Scopelianos, Alachua, FL (US); Robert C. Diluccio, Alachua, FL (US)

(73) Assignee: Axogen Corporation, Alachua, FL (US)

( * ) Notice: Subject to any disclaimer, the term of this patent is extended or adjusted under 35 U.S.C. 154(b) by 527 days.

(21) Appl. No.: 18/051,431

(22) Filed: Oct. 31, 2022

(65) Prior Publication Data

US 2023/0201577 A1     Jun. 29, 2023

Related U.S. Application Data

(60) Provisional application No. 63/266,074, filed on Dec. 28, 2021.

(51) Int. Cl.
*A61N 1/05* (2006.01)
(52) U.S. Cl.
CPC .................................. *A61N 1/0558* (2013.01)
(58) Field of Classification Search
CPC .. A61N 1/0558; A61N 1/0556; A61N 1/0551; A61N 1/36; A61N 1/0464; A61N 1/0468; A61N 1/05
See application file for complete search history.

(56) References Cited

U.S. PATENT DOCUMENTS

| | | | |
|---|---|---|---|
| 5,336,231 A | 8/1994 | Adair | |
| 5,593,405 A | 1/1997 | Osypka | |
| 2005/0033285 A1 | 2/2005 | Swanson et al. | |
| 2008/0015409 A1 | 1/2008 | Barlow et al. | |
| 2010/0331883 A1* | 12/2010 | Schmitz | A61B 17/320758 606/279 |
| 2011/0144449 A1 | 6/2011 | Ortiz et al. | |
| 2011/0160723 A1 | 6/2011 | Tullis et al. | |
| 2014/0288384 A1* | 9/2014 | Mulrooney | A61B 5/037 607/116 |
| 2015/0066019 A1 | 3/2015 | Mark et al. | |
| 2017/0173340 A1* | 6/2017 | Gupte | A61N 1/36114 |
| 2019/0216344 A1 | 7/2019 | Kane | |

FOREIGN PATENT DOCUMENTS

CN            113395938 A       9/2021

OTHER PUBLICATIONS

International Search Report and Written Opinion in Application No. PCT/US2022/048416, dated Mar. 27, 2023 (17 pages).

* cited by examiner

*Primary Examiner* — Rex R Holmes
(74) *Attorney, Agent, or Firm* — Bookoff McAndrews, PLLC

(57) ABSTRACT

An electrode apparatus may include a handle, a cannula extending from a distal end of the handle and having at least one lumen, a ground wire extending through the cannula, and an electrode wire extending through the handle and the cannula, the electrode wire being extendable and retractable relative to a distal end of the cannula. The apparatus may also include a hook, provided in the cannula, and being extendable and retractable relative to the cannula.

17 Claims, 18 Drawing Sheets

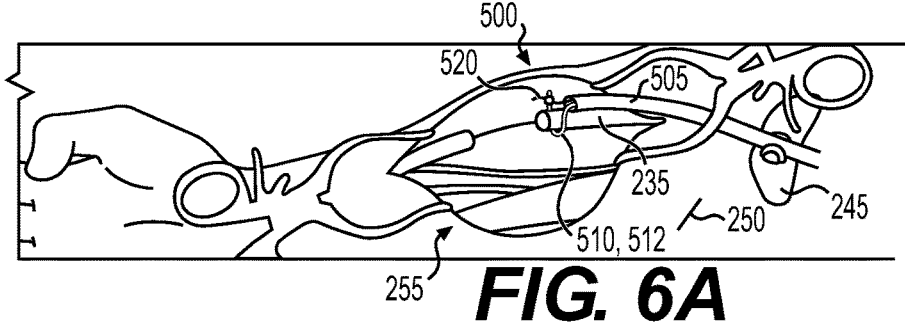
FIG. 6A
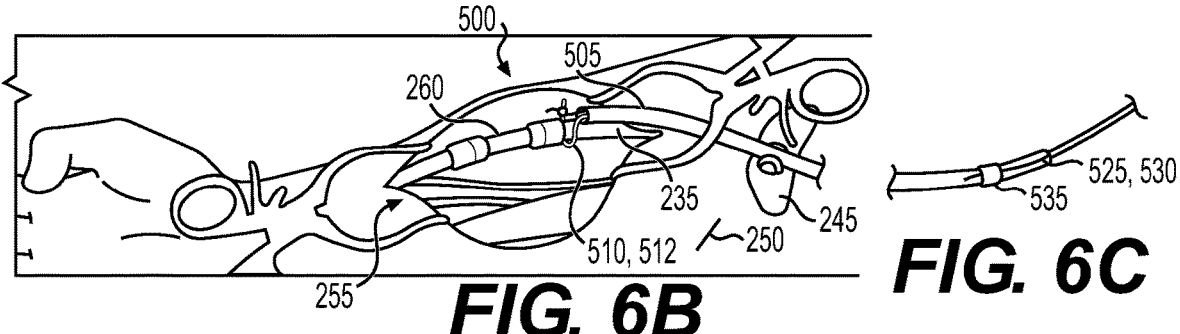
FIG. 6B
FIG. 6C
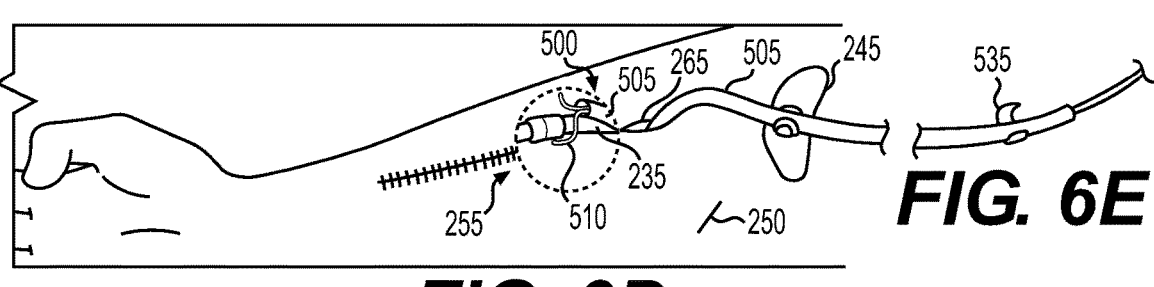
FIG. 6D
FIG. 6E

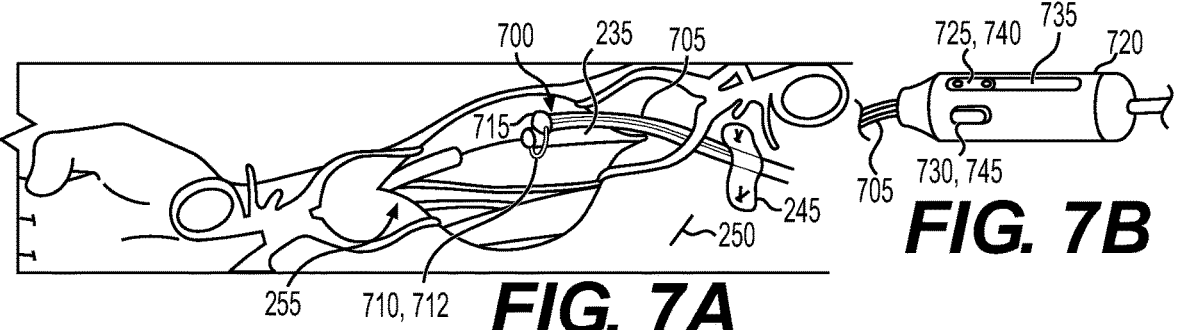
FIG. 7A
FIG. 7B
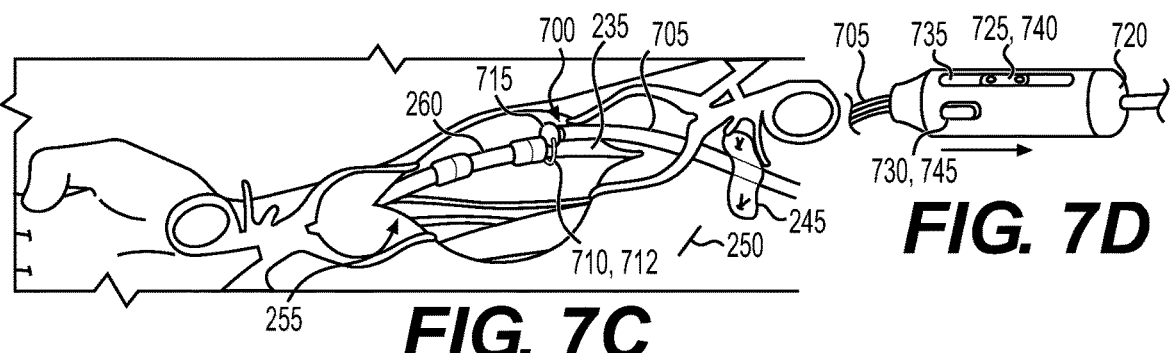
FIG. 7C
FIG. 7D
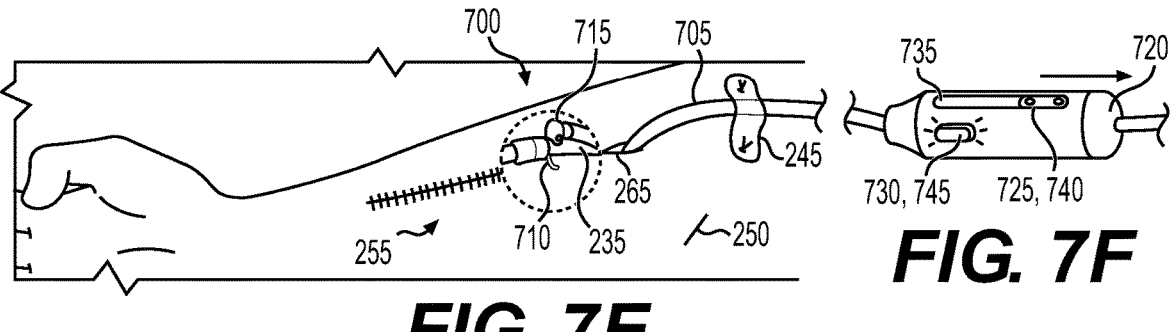
FIG. 7E
FIG. 7F

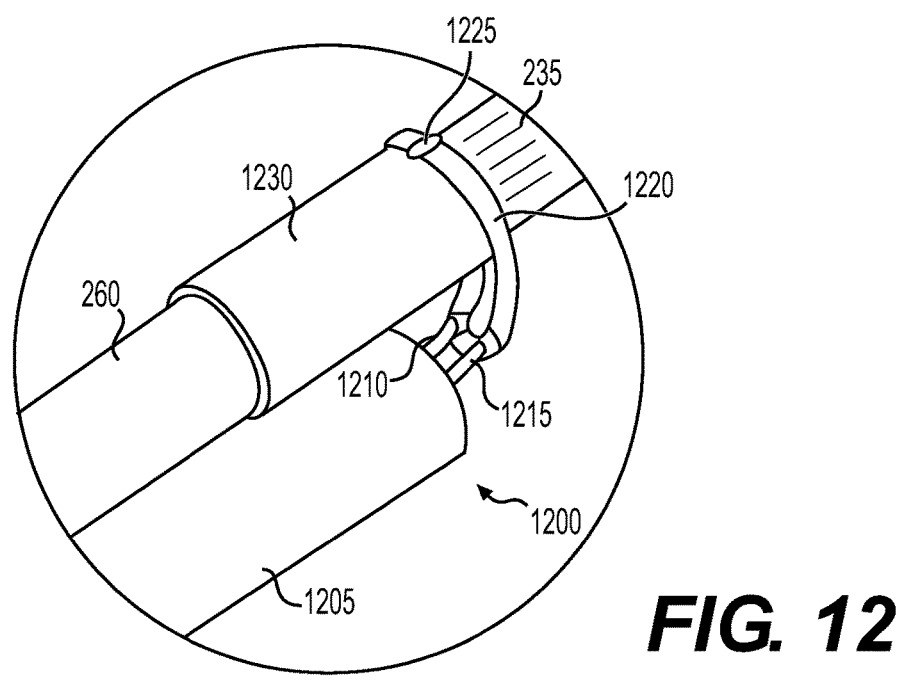
FIG. 12
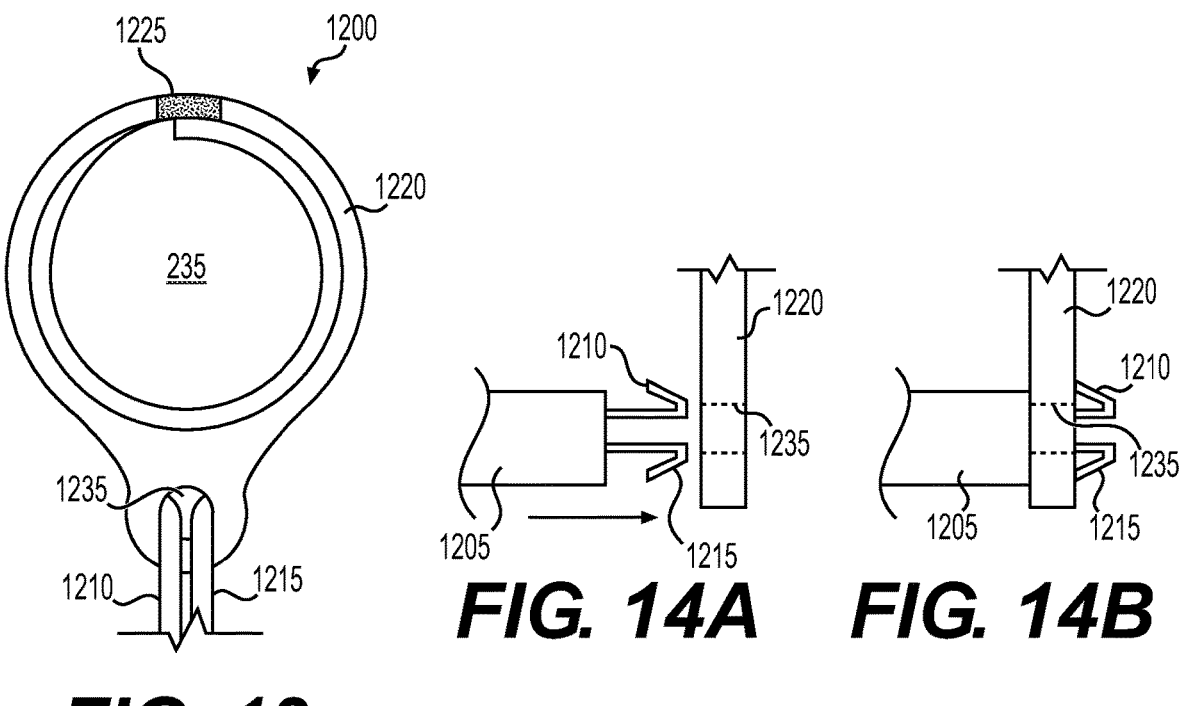
FIG. 13
FIG. 14A
FIG. 14B

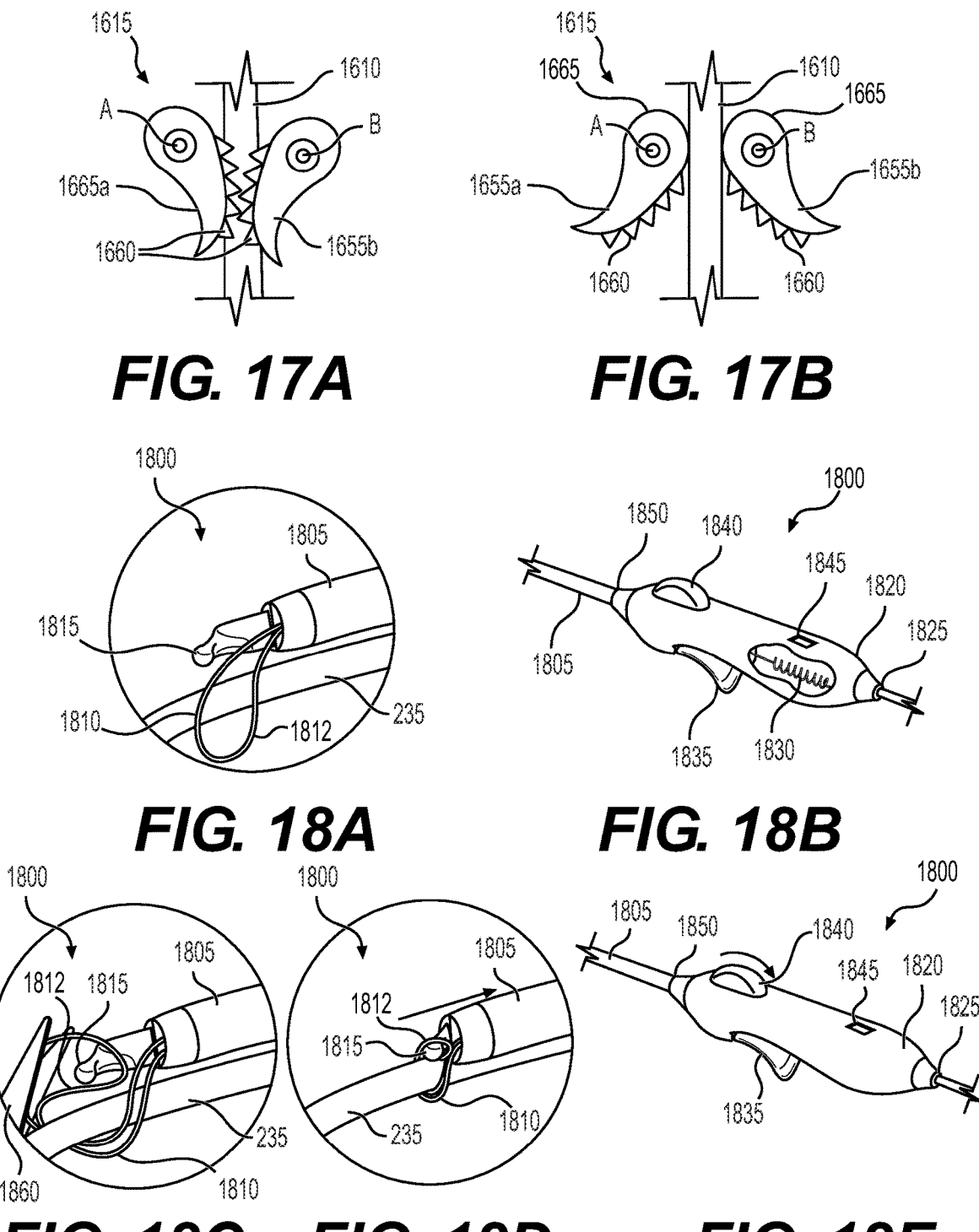
FIG. 17A          FIG. 17B
FIG. 18A          FIG. 18B
FIG. 18C     FIG. 18D          FIG. 18E

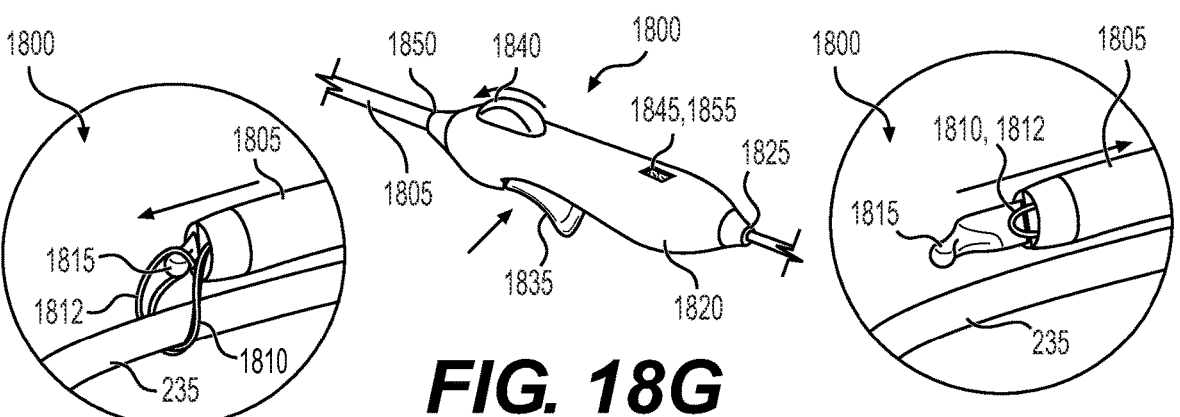
FIG. 18G
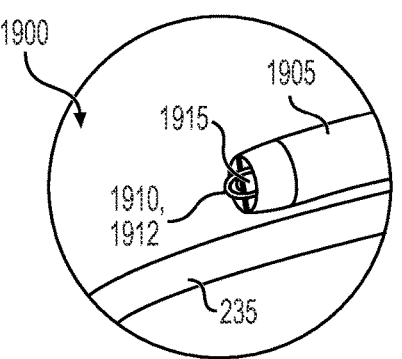
FIG. 18F
FIG. 18H
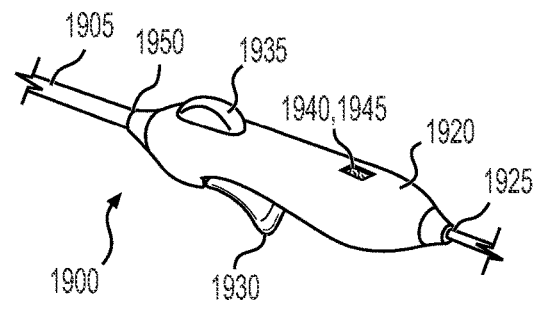
FIG. 19A
FIG. 19B
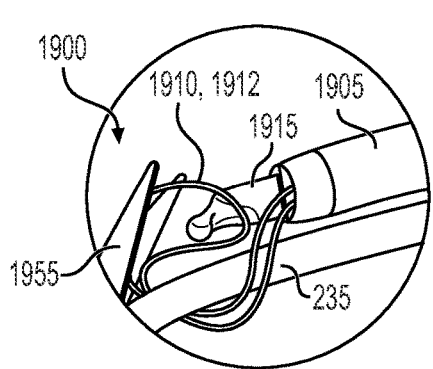
FIG. 19C
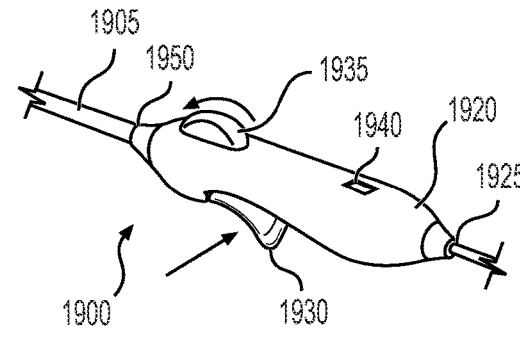
FIG. 19D

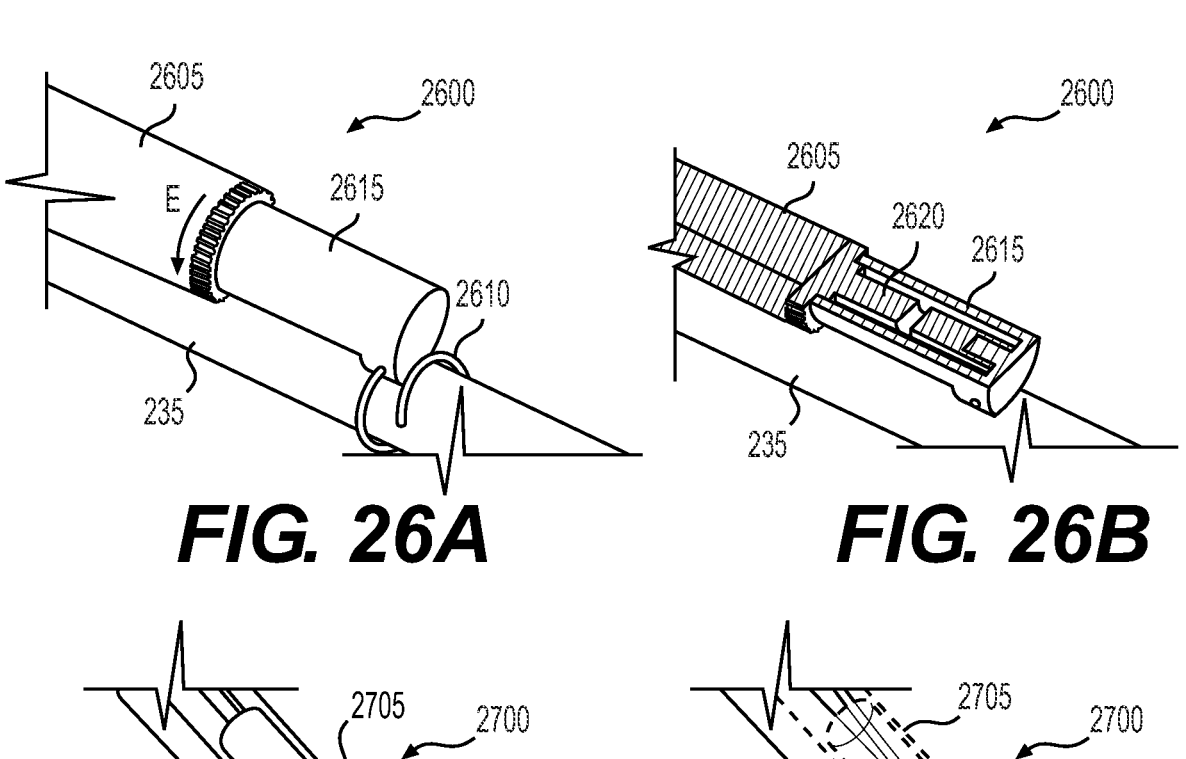
FIG. 26A          FIG. 26B
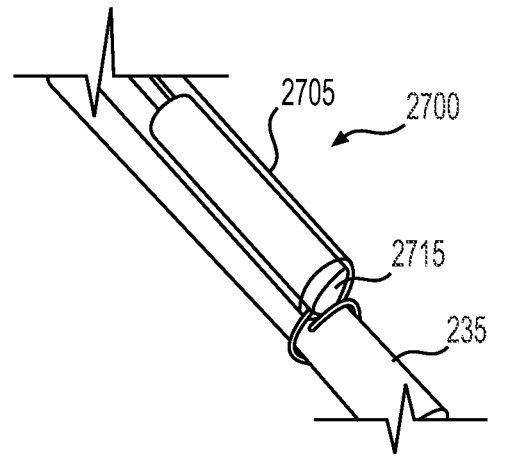
FIG. 27A
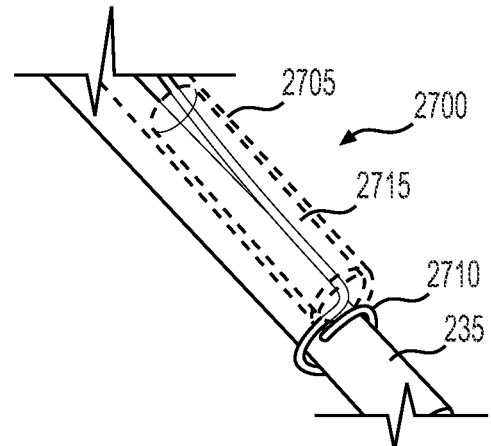
FIG. 27B
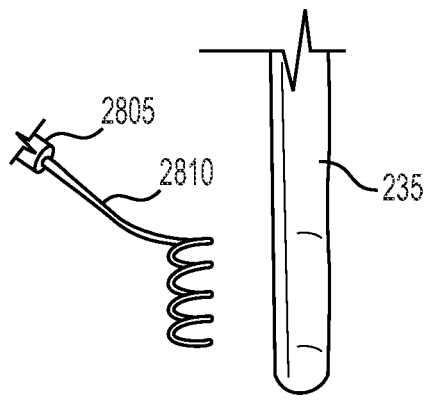
FIG. 28
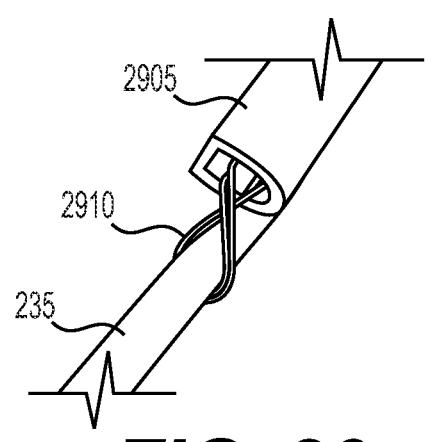
FIG. 29

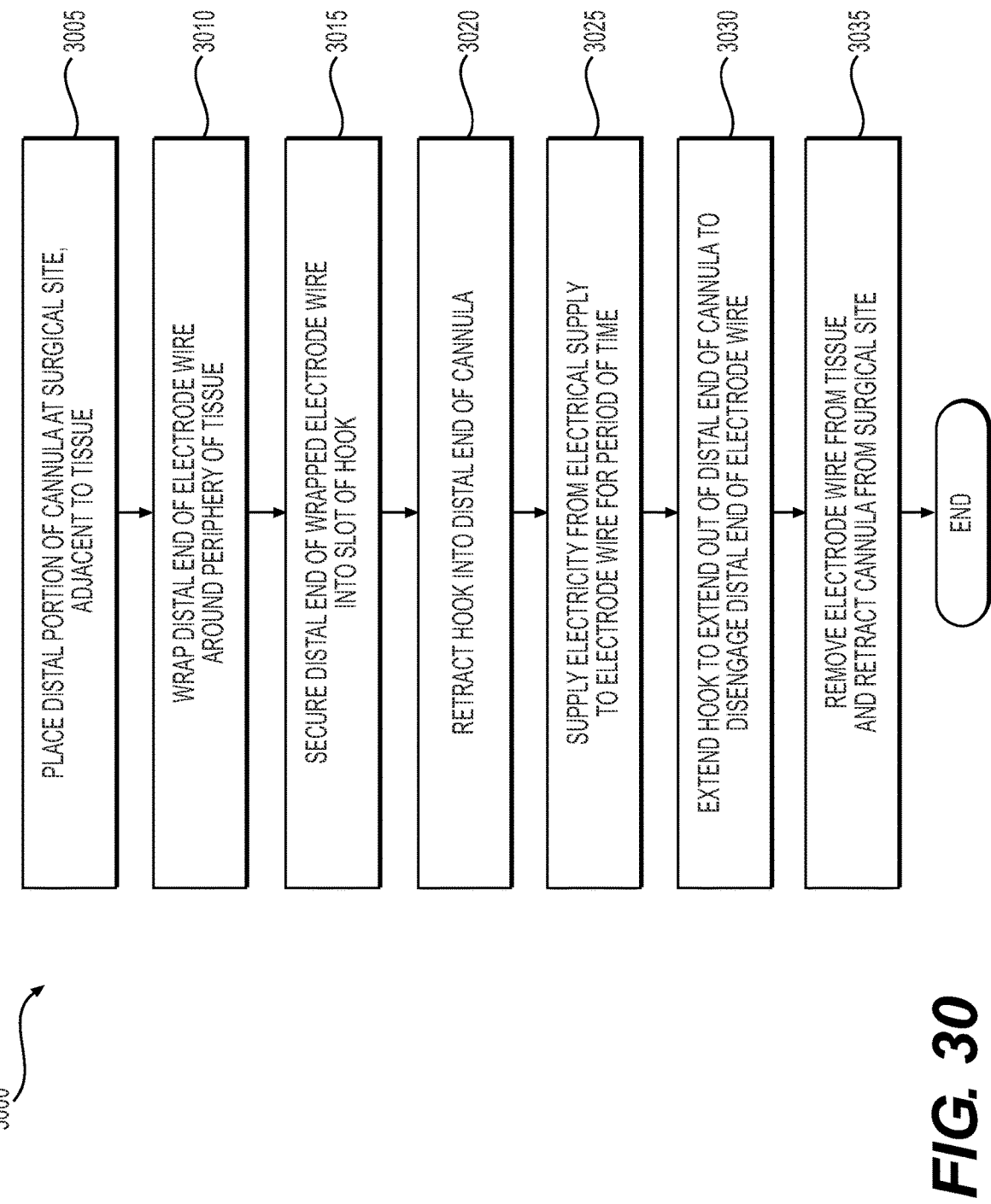

3000

3005 PLACE DISTAL PORTION OF CANNULA AT SURGICAL SITE, ADJACENT TO TISSUE

3010 WRAP DISTAL END OF ELECTRODE WIRE AROUND PERIPHERY OF TISSUE

3015 SECURE DISTAL END OF WRAPPED ELECTRODE WIRE INTO SLOT OF HOOK

3020 RETRACT HOOK INTO DISTAL END OF CANNULA

3025 SUPPLY ELECTRICITY FROM ELECTRICAL SUPPLY TO ELECTRODE WIRE FOR PERIOD OF TIME

3030 EXTEND HOOK TO EXTEND OUT OF DISTAL END OF CANNULA TO DISENGAGE DISTAL END OF ELECTRODE WIRE

3035 REMOVE ELECTRODE WIRE FROM TISSUE AND RETRACT CANNULA FROM SURGICAL SITE

END

3105 — PLACE DISTAL PORTION OF CANNULA AT SURGICAL SITE, ADJACENT TO TISSUE

3110 — WRAP DISTAL END OF ELECTRODE WIRE AROUND PERIPHERY OF TISSUE

3115 — SUPPLY ELECTRICITY FROM ELECTRICAL SUPPLY TO ELECTRODE WIRE FOR PERIOD OF TIME

3120 — REMOVE ELECTRODE WIRE FROM TISSUE, AND RETRACT CANNULA FROM SURGICAL SITE

END

ELECTRODE APPARATUS FOR TISSUE STIMULATION AND RELATED METHOD OF USE

CROSS-REFERENCE TO RELATED APPLICATION

This patent application claims the benefit of priority to U.S. Provisional Patent Application No. 63/266,074, filed on Dec. 28, 2021, the entirety of which is incorporated herein by reference.

TECHNICAL FIELD

Various embodiments of the present disclosure relate generally to an electrode apparatus and, more particularly, to an electrode apparatus for electrical stimulation therapy.

BACKGROUND

Electrical stimulation, or stimming, of tissues may be used to aid in tissue repair. Electrical stimulation therapy, using an electrode apparatus, may be possible during a surgical procedure, by supplying electricity via the electrode apparatus to a tissue subject to treatment while a surgical site, or wound bed, remains open. In order to minimize the duration of a surgical procedure and reduce infection risk at a surgical site, however, the duration of such electrical stimulation therapy may be relatively short. And while it may be possible to continue supply of electrical stimulation therapy following closure of a surgical site by leaving a portion of the electrode apparatus inside a patient, upon expiration of the electrical stimulation therapy, the surgical site will require re-opening to remove the electrode apparatus. This requires that the patient either remain in an operation room or be returned to an operation room for an additional procedure. Further, the re-opening of the surgical site increases the overall duration of the surgical procedure as well as the infection risk.

There is a need, therefore, for an electrode apparatus that allows surgeons to provide electrical stimulation therapy to a tissue during or immediately following a surgical procedure, to continue supply of electrical stimulation after closure of the surgical site, and to easily remove the electrode apparatus upon expiration of the electrical stimulation therapy without requiring re-opening of the surgical site.

The present invention is directed to overcoming one or more of these above-referenced challenges.

SUMMARY OF THE DISCLOSURE

According to certain aspects of the disclosure, an electrode apparatus may include a handle, a cannula extending from a distal end of the handle, wherein the cannula includes at least one lumen therein, a ground wire extending through the cannula, and an electrode wire extending through the handle, and through the cannula, the electrode wire being extendable and retractable relative to a distal end of the cannula. The apparatus may also include a hook provided in the cannula, the hook being extendable and retractable relative to the cannula.

According to other aspects of the disclosure, a method of providing electrical stimulation therapy to a tissue using an electrode apparatus comprising a handle, a cannula extending from a distal end of the handle, an electrode wire extending from an electrical supply and through the cannula, the electrode wire being extendable and retractable relative to a distal end of the cannula, and a hook provided in the cannula, the hook being extendable and retractable relative to the distal end of the cannula, may include placing a distal portion of the cannula in a surgical site, adjacent to the tissue, wrapping a distal end of the electrode wire around a periphery of the tissue, engaging the distal end of the wrapped electrode wire with the hook, retracting the hook, with the electrode wire secured to the hook, into the distal end of the cannula, supplying electricity from the electrical supply to the electrode wire for a period of time, extending the hook, after stopping supply of electricity to the electrode wire, to extend out of the distal end of the cannula, thereby disengaging the distal end of the electrode wire from the slot of the hook, and retracting the cannula from the surgical site.

According to still other aspects of the disclosure, an electrode apparatus may include a handle having a first actuator, a cannula having a proximal end and a distal end, wherein a proximal end of the cannula extends from a distal portion of the handle, a ground wire extending to a distal end of the cannula, wherein the ground wire is configured to connect to an electrical ground, and an electrode wire extending through the cannula, and being extendable and retractable relative to the cannula in response to actuation of the first actuator.

According to yet other aspects, a method of providing electrical stimulation to a tissue using an electrode apparatus comprising a cannula having a proximal end and a distal end, a ground wire extending through the cannula, and an electrode wire extending through the cannula and being extendable and retractable relative to the cannula, may include placing the distal portion of the cannula in a surgical site, adjacent to the tissue, wrapping a distal end of the electrode wire around a periphery of the tissue, supplying electrical stimulation therapy to the tissue for a period of time to promote regeneration of the tissue, removing the electrode wire from the tissue, after stopping supply of electricity to the electrode wire, and retracting the cannula from the surgical site.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIGS. 6A-6E are schematic views of portions of the electrode apparatus shown in FIG. 5 during use.

FIGS. 7A-7F are schematic views of portions of still another exemplary electrode apparatus during use, according to one or more embodiments.

FIG. 12 is a schematic detail view of another exemplary electrode apparatus, according to one or more embodiments.

FIG. 13 is a cross-sectional view of a distal portion of the electrode apparatus shown in FIG. 12.

FIGS. 14A and 14B are detail schematic side views of the distal portion of the electrode apparatus shown in FIGS. 12 and 13.

FIGS. 17A and 17B are schematic detail views of a distal end of the electrode apparatus shown in FIGS. 16A-16H.

FIGS. 18A-18H are schematic views of portions of another exemplary electrode apparatus during use, according to one or more embodiments.

FIGS. 19A-19I are schematic views of portions of still another exemplary electrode apparatus during use, according to one or more embodiments.

FIGS. 20A-20K are schematic views of portions of yet another exemplary electrode apparatus during use, according to one or more embodiments.

FIGS. 21A-21C are schematic views of a cannula with a hook, according to one or more embodiments.

FIGS. 22A-22C are schematic cross-sectional views of the cannula shown in FIG. 21A.

FIGS. 26A and 26B are schematic views of a distal end of an electrode apparatus, with a spool mechanism, according to one or more embodiments.

FIGS. 27A and 27B are schematic views of a distal end of an electrode apparatus, with a coiled electrode wire, according to one or more embodiments.

FIG. 28 is a schematic view of a pre-coiled electrode wire of an electrode apparatus, according to one or more embodiments.

FIG. 29 is a schematic view of an x-looped wire of an electrode apparatus, according to one or more embodiments.

FIG. 30 depicts a flowchart of a method of providing electrical stimulation to a tissue using an electrode apparatus, according to one or more embodiments.

DETAILED DESCRIPTION OF EMBODIMENTS

Figure 1:
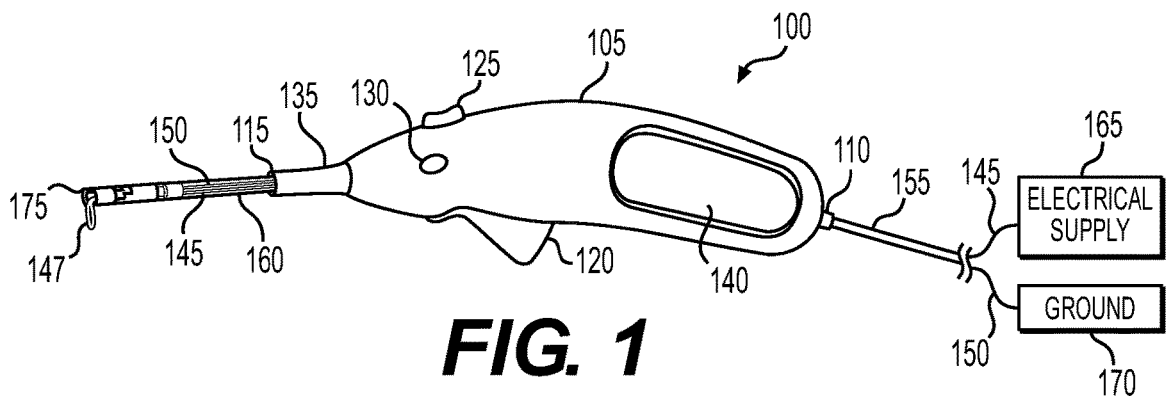
FIG. 1 is a schematic view of an exemplary electrode apparatus, according to one or more embodiments.

Various embodiments of the present disclosure relate generally to electrode apparatuses for use in electrical stimulation therapy, or stimming, during and/or following a surgical procedure.

The singular forms "a," "an," and "the" include plural reference unless the context dictates otherwise. The terms "approximately" and "about" refer to being nearly the same as a referenced number or value. As used herein, the terms "approximately" and "about" generally should be understood to encompass ±10% of a specified amount or value. The use of the term "or" in the claims and specification is used to mean "and/or" unless explicitly indicated to refer to alternatives only or the alternatives are mutually exclusive, although the disclosure supports a definition that refers to only alternatives and "and/or." As used herein "another" may mean at least a second or more. As used herein, the terms "comprises," "comprising," "including," "having," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." In addition, the term "between" used in describing ranges of values is intended to include the minimum and maximum values described herein. The term "proximal" is used to describe the end of a device that is located closest to an operator of the device when using a device on a subject, whereas the term "distal" is used to describe the end of a device that is located closest to a subject on whom the device is being used and farthest away from the operator.

The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed.

Embodiments of the disclosure are generally drawn to electrode apparatuses including an electrode that can be placed in contact with a tissue—for example, wrapped around a portion of the tissue—during surgery and then removed from the tissue after closure of the surgical site. Example apparatuses may include an electrode portion for contacting the tissue at a distal end of the apparatus, a cannula into which the electrode may be retracted into when positioning the cannula in the patient and/or removing the electrode after surgery, and a handle operably coupled to the electrode and the cannula for controlling application and removal of the electrode during use.

Examples of tissue with which the electrode apparatuses may be used include nerve tissue, such as peripheral nerve tissue or central nervous system tissue. Other types of tissue suitable for the present disclosure include, but are not limited to epithelial tissue, conductive tissue, muscular tissue, capillary tissue, dermal tissue, smooth muscle tissue, and cardiac tissue. In other aspects, electrode apparatuses for applying electrical stimulation therapy may be used on tissue grafts, which may be synthetic or non-synthetic nerve grafts, or human or animal nerve grafts. For example, the tissue may be mammalian tissue, including human tissue and tissue of other primates, rodent tissue, equine tissue, canine tissue, rabbit tissue, porcine tissue, or ovine tissue. In addition, the tissue may be non-mammalian tissue, selected from piscine, amphibian, or insect tissue. The tissue may be allogeneic or xenogeneic to a subject into which the graft is implanted. The tissue may be a synthetic tissue, such as, but not limited to, laboratory-grown or 3D-printed tissue.

FIG. 1 shows an example of a handle portion 105 that may be included in an exemplary electrode apparatus 100. It is recognized that handle portion 105 as described herein may be modified with any combination of actuators (e.g., thumb-wheels, levers, triggers, knobs, buttons, slides, or any other mechanisms) suitable for controlling insertion of the device, including extension of the distal electrode used to stimulate the tissue from the cannula, attachment of the electrode to the tissue, removal of the electrode from the tissue, and/or retraction of the electrode within the cannula. Though an example handle portion 105 is depicted with specific actuators, it is understood that handle portion 105 may be modified depending on the arrangement, method of attachment, and/or method of release of a distal electrode for applying stimulation. Specific examples of handles 105 suitable for use in conjunction with other embodiments of electrode apparatuses are described further below.

Handle portion 105 may be configured to control a distal end of electrode apparatus 100, and may include an inlet 110 at a proximal end, an outlet 115 at a distal end, a trigger mechanism 120, a slide mechanism 125, a lock-out mechanism 130, a strain relief mechanism 135, and a spring-loaded clip mechanism 140. In some aspects, the handle portion 105 may have an ergonomic shape and may be relatively light-weight, so as to comfortably fit within a hand of a user and to provide the user with adequate control of the electrode apparatus 100.

An electrode wire 145 and a ground wire 150 extend through a lumen 155 to the inlet 110 of the handle portion 105, and through a cannula 160 located within the handle portion 105 and extending distally from the outlet 115 of the handle portion 105. A proximal end of the electrode wire 145 is shown electrically connected to an electrical stimulation platform, or electrical supply 165, discussed in more detail below, and a proximal end of the ground wire 150 is shown electrically connected to an electrical ground 170. The electrode wire 145 extends through cannula 160 and, in some embodiments, may form a loop 147 at a distal end thereof. In addition, in some embodiments, the distal end of the cannula 160 may have a hook 175 for selectively controlling the electrode wire 145. For example, hook 175 may aid in attaching electrode wire 145 with the tissue, or removing or retracting the electrode wire 145 at the end of the treatment. Embodiments of the distal end of electrode apparatus 100 will be discussed in further detail below.

The trigger mechanism 120 may be used to extend and retract the hook 175, and is therefore mechanically coupled to the hook 175 within the handle portion 105, as described below with respect to FIG. 2. The slide mechanism 125 may be used to loosen and tighten the electrode wire 145, and is therefore mechanically coupled to the electrode wire 145, as described below with respect to FIG. 2. Although a slide mechanism is depicted in FIG. 1, a thumbwheel or other appropriate actuation mechanism may be incorporated at location 125 of handle portion 105. The strain relief 135 may be included to provide reinforcement and protection to a connection between the cannula 160 and the handle portion 105. The lock-out mechanism 130 may inhibit movement of the slide mechanism 125, as may be desired once the electrode wire 145 is tightened around a tissue, as will be described further below, to prevent overtightening of the electrode wire 145, which could damage the tissue. The spring loaded clip 140 is optionally provided on an exterior surface of the handle portion 105, and may allow a surgeon to clip the electrode apparatus to the patient, e.g., via clipping onto a gown worn by a patient or onto another suitable location, following placement of the apparatus 100. The spring loaded clip 140 may promote portions of the apparatus 100 placed within the patient (described in more detail below) remaining in place within the patient until removal of the apparatus 100.

Figure 2:
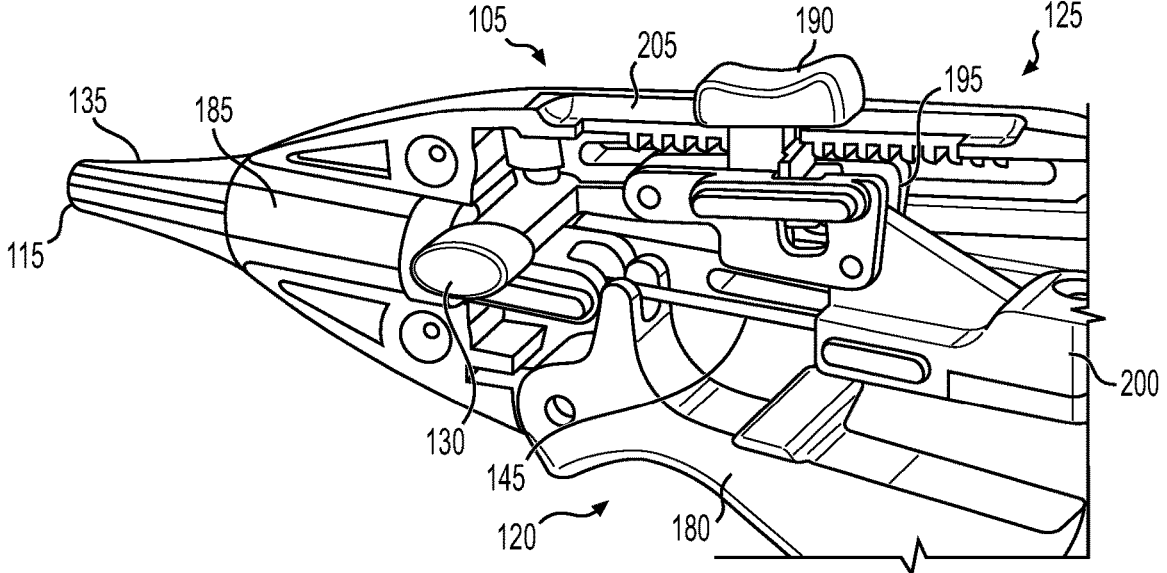
FIG. 2 is a cutaway schematic view of a handle portion of the exemplary electrode apparatus shown in FIG. 1, according to one or more embodiments.

FIG. 2 is a cutaway view of the handle portion 105 of the electrode apparatus 100 shown in FIG. 1. In particular, FIG. 2 shows the trigger mechanism 120, in which a trigger 180 is mechanically connected to the hook 175 via a pusher rod 185 to push and pull the electrode wire 145. In this embodiment, when the trigger 180 is compressed or pulled, the pusher rod 185 extends distally to cause the hook 175 to protrude from the distal end of the cannula 160, and when the trigger 180 is released, the pusher rod 185 withdraws in a proximal direction to retract the hook 175. The slide mechanism 125 includes a slider 190 that is mechanically connected to the electrode wire 145 by actuators 195, 200, to provide slack or tension to the electrode wire 145. The slider 190 is movable within a slot 205 provided in the handle portion 105. The slider 190 is configured to move between an initial position, which may be approximately ⅓ back from a forward, or distal-most, position within the slot 205, a cinching position, which may be approximately ⅔ back from the forward position, and the forward position, in which the slider 190 moves to a distal end of the slot 205. When the slider 190 is in the initial position, the electrode wire 145 is relatively loose or slack, such that a distal end of the electrode wire 145 may be manipulated or bent and wound around a tissue. When the slider 190 is in the cinching position, the electrode wire 145 has a set amount of tension, such that the electrode wire 145 contacts all, sub-stantially all, or some of a circumferential surface of the tissue. And when the slider 190 is in the forward position, the electrode wire 145 is loosened, potentially more so relative to the amount of slack of the electrode wire 145 in the initial position, so that the electrode wire 145 may be disengaged to unwrap from the tissue. The lock-out mecha-nism 130 locks the slider 190 in position, which may be the initial position, the cinching position, or the forward portion, to prevent over-tightening or inadvertent movement of the electrode wire 145.

Figure 3:
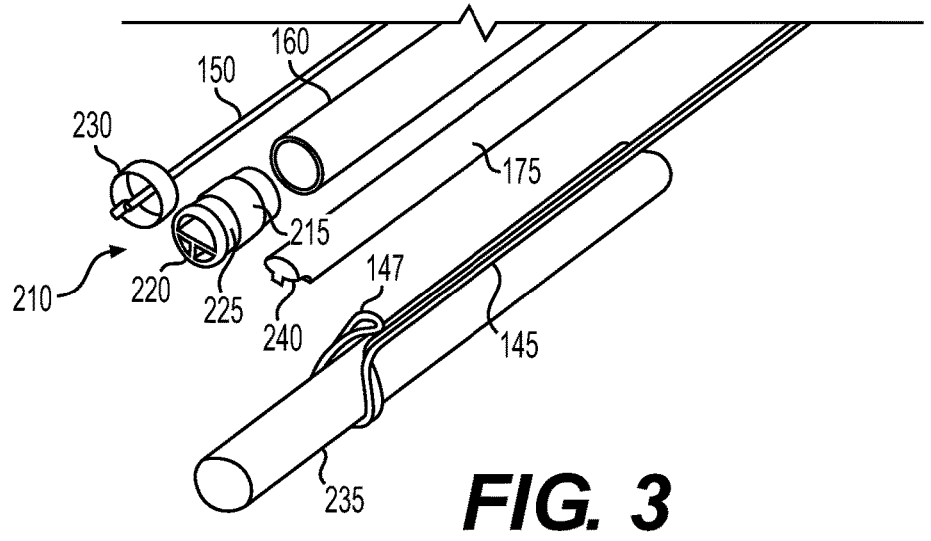
FIG. 3 is a schematic view of elements of an exemplary electrode apparatus, according to one or more embodiments.

FIG. 3 shows elements suitable for the distal end of the electrode apparatus 100, according to one or more embodi-ments. In particular, FIG. 3 shows the cannula 160, which has a rounded, e.g., circular, cross-sectional shape. A length of the cannula 160 may be within a range of about 18 inches to about 3 feet (or about 457.2 mm to about 914.4 mm), and an outer diameter of the cannula 160 may be in a range of about 0.5 mm to about 5.1 mm. The cannula 160 may be formed of a biocompatible material, for example, polyure-thane (PU), polytetrafluoroethylene (PTFE), polyolefins, crosslinked poly(vinyl acetate), and/or silicone. The cannula 160 may also be a single lumen cannula or a multi, e.g., dual, lumen cannula. Within a distal portion of the cannula 160, an insert 210 may be provided, which may be PU, PTFE, polyolefins, crosslinked poly(vinyl acetate), and/or silicone. The insert 210 may have a protruding portion 215 to provide an interference fit between the insert 210 and the cannula 160 when the insert 210 is inserted into the distal portion of the cannula 160. The insert 210 may also have a T-shaped divider 220 at a distal end thereof, through which different elements, e.g., the ground wire 150, the electrode wire 145, and the hook 175, may be inserted. The divider 220 may have other shapes, as discussed in more detail below. The insert 210 may also have a circumferential slot 225, proximal to the circumferential protruding portion 215, into which a ground ring 230 may be inserted. The ground ring 230 is attached to a ground wire 150 that extends through a portion of the insert 210 and through the cannula 160 to an electrical ground 170 (FIG. 1). FIG. 3 also shows an electrode wire 145, wrapped around a tissue 235. The ground ring 230 and the ground wire 150 provide electrical continuity through the electrode apparatus 100, from an electrical stimulation platform 165 to an electrical ground 170 at a proximal end of the ground wire 150.

The electrode wire 145 is shown in a looped configuration, meaning the electrode wire 145 extends from a distal end of cannula 160, and upon extension beyond a distal end of the cannula 160, turns or loops, and returns back toward the distal end, making a second pass through the cannula 160. The loop 147 formed at the distal end of the electrode wire 145 may be secured using one of the mechanisms described herein (e.g., a hook, a ball, etc.). Although a looped embodiment of electrode wire 145 is shown in FIG. 3, a non-looped embodiment, as described herein, may be included. For example, the electrode wire 145 may be a single or non-looped electrode wire that extends from a proximal end, connected to the electrical stimulation platform 165, to a distal end that extends beyond the distal end of the cannula 160. A length of the electrode wire 145 may be set depending on a size, and in particular, a diameter, of a tissue 235 around which the electrode wire 145 is to be wound, and depending on the particular configuration of the electrode wire 145 (e.g., looped vs. not looped). The length of the electrode wire 145 may be selected to ensure the electrode wire 145 is long enough to wrap around a tissue 235 having a diameter ranging, e.g., from about 1 mm to about 20 mm, about 1 mm to about 12 mm, about 1-5 mm, or about 7-12 mm.

The electrode wire 145 may be a stranded, flexible wire, as discussed relative to certain embodiments below. A relatively flexible electrode wire 145 may be easier to manipulate for wrapping around tissue 235 and for tensioning of the electrode wire 145 once it has been wrapped around the tissue 235. The electrode wire 145 may be formed, for example, of a shape memory material, such as Nitinol®, or a non-shape memory material, such as copper, annealed copper, copper coated in gold, or copper with gold plating. The material may be "off-the-shelf," or the material may be customized, formed of common wire materials, but formed to particular specifications regarding materials, length, number of strands, and/or thickness of strands. One or more portions of electrode wire 145 may be insulated, including, for example, proximal portions not configured for contact with tissue 235. A distal portion of electrode wire 145 may not include insulation, and, e.g., may be stripped of an insulation layer. In some embodiments, a portion, e.g., a distal tip, of the uninsulated distal portion of electrode wire 145 may be soldered using, for example, a biocompatible material, such as a material described in Durisin et al., "Development and Characterisation of New Biocompatible Sn—Mg Lead-Free Solder," Journal of Metastable and Nanocrystalline Materials, Vol. 31, pp. 6-10 (2019).

In addition, while the electrode wire 145 may be shown or described in some embodiments as providing 360° of conduction or connection to tissue 235 by virtue of the electrode wire 145 being wrapped 360° around a circumferential surface of the tissue 235, the electrode apparatus 100 described herein may provide sufficient electrical stimulation with only 50% of conduction or connection to the tissue 235 (that is, even if the electrode wire 145 wraps only 180° around the circumferential surface of the tissue 235, the electrode apparatus 100 may still provide sufficient electrical stimulation). Further, as discussed in more detail below, depending on the particular embodiment, the electrode wire 145 may be secured to a tissue 235, such as a nerve, that is intact or that is severed (for example, a nerve end). In addition, the electrode wire 145 may be secured to the tissue 235 before or after placement of a tissue graft. No internal securement to the tissue 235 may be required, rather the electrode wire 145 may only be externally secured to the tissue 235.

The hook 175 may be integrally formed with the pusher rod 185, and may have a rounded distal end to prevent damage to tissue 235. In addition, the hook 175 may have a protrusion 240 on one surface for grasping a distal end or a loop 147 of the electrode wire 145. One or more surfaces of the hook 175 may have a bevel. A stroke of the pusher rod 185 (FIG. 2), representing a distance the hook 175 moves from an extended position to a retracted position, may be determined based, at least in part, on a size, e.g., a diameter, of the tissue 235 around which the electrode wire 145 is to be wrapped. For example, the pusher rod 185 may have a stroke of about 19.5 mm for a tissue 235 having a diameter of about 1 mm to about 5 mm, and a stroke of about 41 mm for a tissue 235 having a diameter of about 12 mm. Alternatively, the pusher rod 185 may have a stroke of about 25 mm for a tissue 235 having a diameter of about 5 mm, or about 45 mm for a tissue 235 having a diameter of about 12 mm.

In some embodiments, the insert 210 may be a cowling, having an opening for the electrode wire 145, and having a closed distal face, which acts as a stop for the electrode wire 145. In an embodiment in which the insert 210 is in the form of a cowling, a portion of the electrode wire 145 that extends beyond the distal end of the cannula 160 may have insulation in order to improve cinching. Insulation may alternatively be removed from the portion of the electrode wire 145 that extends beyond the distal end of the cannula 160, to ensure interaction between conductive portions of the wire 145 and tissue 235. Alternatively, the distal tip of the cannula 160 may not include a cowling, and the electrode wire 145 may have a welded tip without insulation. In such an embodiment, the electrode wire 145 extends beyond, or distal relative to, the hook 175, and may be shaped to improve cinching. For example, the electrode wire 145 may have a small ball welded to a distal end thereof, which may act as a catch for the hook 175.

The electrical stimulation platform 165 may have a voltage in a range of about 1 V to about 10 V, and more specifically, about 3 V to about 5 V, and a current in a range of about 0.0 mA to about 13.3 mA, and more specifically, about 0.25 mA to about 0.5 mA. The current may be supplied in square wave pulses at a pulse width in a range of about 0 μs to about 1500 μs, and more specifically, about 100 μs to about 250 μs, and a frequency in a range of about 3 Hz to about 20 Hz. The duty cycle may be in a range of about 25% to about 75%, and, in particular, may be about 50%. The duration of the electrical stimulation process may be in the range of about 1 minute to about 60 minutes, and may be monophasic. The power supply needed for the electrical stimulation platform may be a 3 volt direct current "wall wart" supply. An expected resistance load is in a range of about 10.7 kΩ2±5 kΩ.

Figures 4A, 4B, 4C, 4D, 4E, 4F, 5:
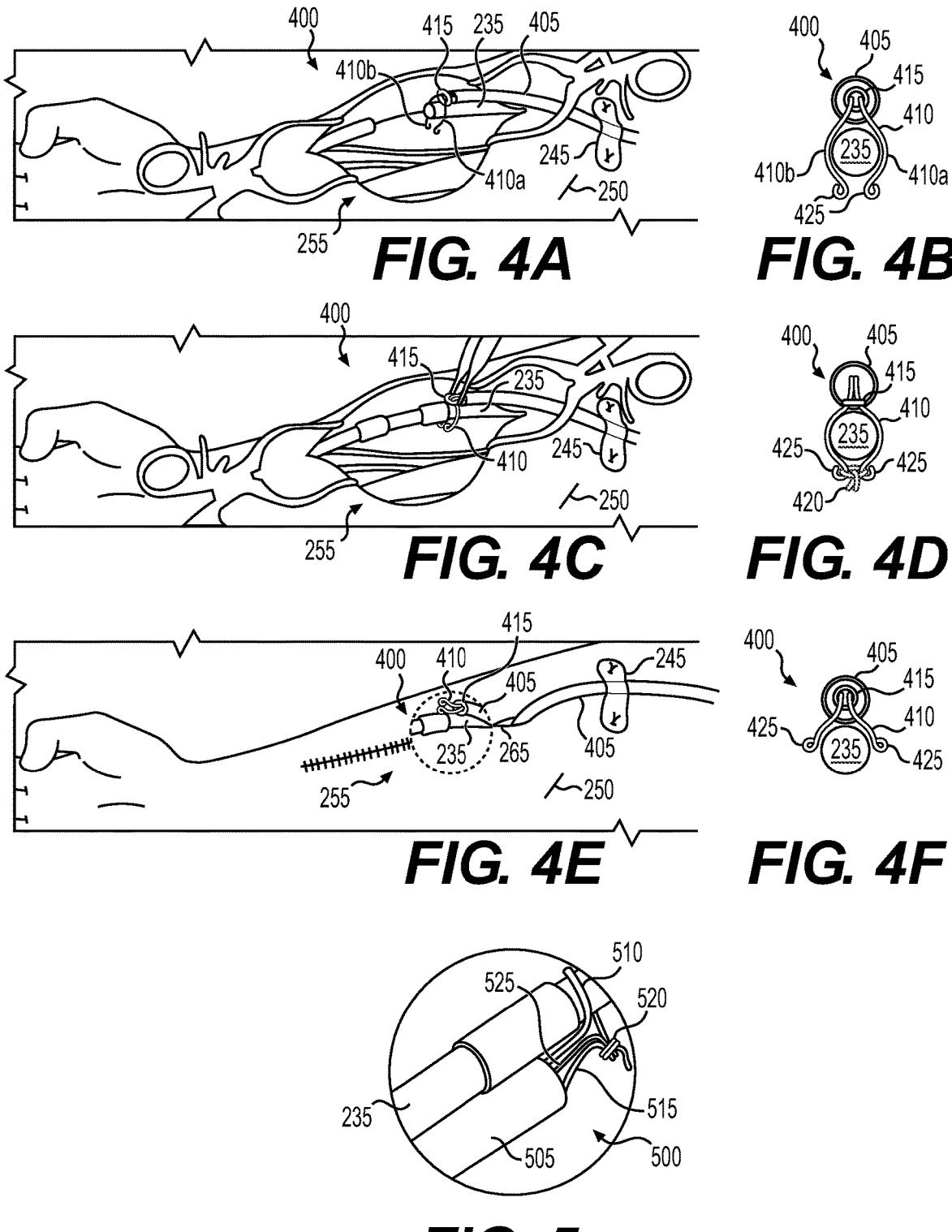
FIGS. 4A-4F are schematic views of portions of an exemplary electrode apparatus during use, according to one or more embodiments.
FIG. 5 is a detail view of a distal end of another exemplary electrode apparatus, according to one or more embodiments.

In addition, as shown in at least FIGS. 4A, 4C, and 4E, for example, the electrode apparatus 100 may be used with an adhesive skin tab 245, which may hold the cannula 160 in place on skin 250 of a patient near the surgical site 255, while the electrode wire 145 remains in place during electrical stimulation therapy. In addition or alternatively, one or more of sutures, bands, adhesives, or hook-and-loop fasteners (e.g., Velcro) may be used to secure and stabilize the cannula 160 on the skin 250 of the patient.

FIGS. 4A-4F show an electrode apparatus 400 including an electrode wire 410 that has two branches configured to wrap around tissue 235, according to an embodiment. Electrode apparatus 400 may include a cannula 405, an electrode wire 410 extending beyond a distal end of the cannula 405, an O-ring 415, and a dissolvable suture 420 at a distal end thereof. The electrode apparatus 400 includes other features not shown in FIGS. 4A-4F, including, for example, a handle portion and a ground wire. FIG. 4A shows placement of the electrode apparatus 400 within a surgical site 255. In particular, a distal end of the electrode wire 410 is split into two branches 410a and 410b, each having a ferrule 425 at a distal end thereof, with the dissolvable suture 420 being attached to the ferrules 425, as shown in FIG. 4D. Ferrules 425 may provide a structural element to attach suture 420 to, and may be attached to or integrally formed with branches 410a, 410b. Here, the term "dissolvable" indicates that the material used to form the dissolvable suture 420 is absorbable into the human body. In an alternative embodiment, instead of a split electrode wire 410, the electrode wire 410 and a ground wire may form two leads extending from a distal end of the cannula. In such an embodiment, distal tips of the electrode wire 410 and the ground wire may be insulated to promote the flow of electrical current across the tissue 235, rather than down the wires.

During use, the cannula 405 is placed adjacent to a tissue end, and the branches 410a, 410b of the electrode wire 410 are placed around the tissue 235. Although electrode wire 410 is shown in conjunction with a tissue graft 260 inserted between two portions of severed tissue 235, electrode wire 410 may be used in conjunction with two ends of severed tissue 235 rejoined without the use of a graft 260, or may be used with a tissue 235 that is not severed, since branches 410a, 410b may be wrapped around tissue 235 prior to application of dissolvable suture 420. If used in conjunction with severed tissue 235, branches 410a, 410b may be applied either before or after placement of a tissue graft 260, or reconnection with an end of severed tissue 235. FIG. 4B shows placement of the O-ring 415 around a portion of the branches 410a, 410b of the electrode wire 410, and engagement of the dissolvable suture 420 at ends of the ferrules 425, thereby securing the electrode wire 410 to the tissue 235. In one embodiment, the dissolvable suture 420 may be pre-tied and the electrode wire 410 can be placed around the tissue 235 prior to placement of a tissue graft 260. O-ring 415 may be cinched over branches 410a, 410b to fit branches 410a, 410b to the tissue 235 once in place.

Once the electrode wire 410 is secured to the tissue 235, electrical stimulation therapy may begin. Then, the surgical site 255 may be closed before, during, or after commencement of electrical stimulation therapy, with a small opening 265 remaining, shown in FIG. 4E, through which the cannula 405 passes while electrical stimulation therapy continues. In other aspects, electrical stimulation therapy may begin once the surgical site 255 is closed. Upon completion of electrical stimulation therapy, and once the suture 420 has dissolved, the electrode wire 410 is disengaged from the tissue 235, the electrode wire 410 may be retracted into cannula 405, and the cannula 405 and the electrode wire 410 may be retracted or withdrawn through the small opening 265. FIGS. 4E and 4F show disengagement of the electrode wire 410 upon dissolution of the suture 420, which allows the electrode wire 410 and the cannula 405 to be removed from the surgical site 255.

The dissolvable suture 420 of the electrode apparatus 400 shown in FIGS. 4A-4F may be formed of an absorbable material, such as monomers, polymers, and copolymers, including, for example, materials derived from one or more of the following monomers: e-caprolactone, l-lactide, glycolide, p-dioxanone, and trimethylene carbonate. Other materials may include polymers, such as phenol polymers derived from tyrosol and/or other analogs, or diphenolic monomers derived from tyrosine and/or tyrosine analogs. Exemplary polymers are described, for example, in U.S. Pat. Nos. 9,416,090 B2, and 9,416,090 B2, which are herein incorporated by reference in their entireties.

Still further, the material may include poly-vinyl alcohol, hyaluronic acid, or modified hyaluronic acids. Benefits of the embodiment shown in FIGS. 4A-4F include minimal to no new surgical techniques required for implantation of the electrode apparats 400 (e.g., only suture 420 may need to be applied, if not pre-set), no custom application or removal tools may be required, and the electrode apparatus 400 may be capable of providing nearly 360° of conduction to the tissue 235. This embodiment may allow a surgeon to establish an amount of compression on the tissue 235 based on a tightness with which the suture 420 is secured to the ferrules 425. This embodiment may also provide for an electrode apparatus 400 that may be implanted during a surgical procedure, may remain in place after closure of a surgical site, e.g., while a patient is in recovery, to continue electrical stimulation therapy, and may be easily removed upon completion of the electrical stimulation therapy, without requiring additional surgical processes or resources.

FIGS. 5 and 6A-6E depict an electrode apparatus 500 according to another embodiment in which electrode wire 510 is applied to tissue 235 via a releasable knot 520. FIG. 5 is a detail view of the electrode apparatus 500, showing a cannula 505, an electrode wire 510, a ground wire 515, and a releasable knot 520 formed from a filament 525, including two cords, at a distal end of the electrode apparatus 500. The electrode apparatus 500 includes other features not shown in FIGS. 5 and 6A-6E, including, for example, a handle portion. The releasable knot 520 may be, for example, a quick-release slip knot. The electrode apparatus 500 may be provided with a pre-tied releasable knot 520, or releasable knot 520 may be tied during the procedure by a person applying electrode wire 510, and the knot 520 may be released from outside of a surgical site 255, via a proximal end 530 of the filament 525, shown in FIG. 6C, to detach the electrode wire 510 from the tissue 235.

FIGS. 6A-6E are schematic views of the electrode apparatus 500 shown in FIG. 5 in use. FIG. 6A shows placement of the electrode apparatus 500 within a surgical site 255. The cannula 505 is placed adjacent to a tissue requiring treatment, and a loop 512 formed by the electrode wire 510 is placed around the tissue 235, before placement of a tissue graft 260, or prior to bringing ends of a transected tissue 235 together, in a case in which no tissue graft 260 is used. FIG. 6B shows securing of the looped electrode wire 510 using the releasable knot 520. FIG. 6B also shows placement of an adhesive skin tab 245 on skin 250 of the patient, to secure the cannula 505 in position, thereby preventing movement of the cannula 505 during electrical stimulation therapy. During implantation, a proximal end 530 of filament 525 may be secured in place by, e.g., a tab 535 to inhibit accidental tightening or releasing of knot 520. Once the tissue graft 260 is in place, the releasable knot 520 may be tightened by pulling on the proximal end 530 of one of the cords of the filament 525, shown in FIG. 6C, which tightens the electrode wire 510 around the tissue 235 to promote contact between the electrode wire 510 and the tissue 235. A tab 535 may be provided near the proximal end 530 of the filament 525, to limit an amount by which the filament 525 may be pulled for tightening. This limit is to ensure the filament 525 is not pulled too far and does not damage the tissue 235. Although electrode wire 510 is shown in conjunction with a tissue graft 260 inserted between two portions of severed tissue 235, electrode wire 510 may be used in conjunction with two ends of severed tissue 235 rejoined, without the use of a graft 260, or may be used with a tissue 235 that is not severed, since the electrode wire 510 may be wrapped around tissue 235 prior to tying of the releasable knot 520. If used in conjunction with severed tissue 235, the releasable knot 520 may be tied either before or after placement of a tissue graft 260, or reconnection with an end of severed tissue 235. In some aspects, releasable knot 520 may be pre-tied, so that a surgeon is able to simply slide the electrode wire 510 around a transected portion of tissue.

Once the electrode wire 510 is secured to the tissue 235, electrical stimulation therapy may begin. Then, the surgical site 255 may be substantially closed before, during, or after commencement of electrical stimulation therapy, with a small opening 265 remaining through which the cannula 505 passes while electrical stimulation therapy continues. In other aspects, electrical stimulation therapy may begin once the surgical site 255 is closed. Upon completion of electrical stimulation therapy, the electrode wire 510 is disengaged by pulling on the proximal end 530 of the other cord, of the two cords that form the filament 525, thereby releasing the releasable knot 520, while removing the tab 535, to untie or release the knot 520, as shown in FIGS. 6D and 6E. Then, the cannula 505 and the electrode wire 510 are retracted or withdrawn through the small opening 265.

The electrode apparatus 500 of the embodiment shown in FIGS. 5 and 6A-6E may provide positive feedback that the electrode wire 510 has been disengaged from the tissue 235 by virtue of the filament 525 being pulled, thereby releasing the knot 520. Further, the electrode apparatus 500 of this embodiment may not require custom tools for application or removal of the apparatus 500. The electrode apparatus 500 may also provide up to 360° contact between the electrode wire 510 and the tissue 235. This embodiment also provides for an electrode apparatus 500 that may be implanted during a surgical procedure, may remain in place after closure of a surgical site, e.g., while a patient is in recovery, to continue electrical stimulation therapy, and may be easily removed upon completion of the electrical stimulation therapy, without requiring additional surgical processes or resources.

FIGS. 7A-7F show an electrode apparatus 700 according to another embodiment that has a single electrode wire 710 that protrudes distally from cannula 705 and then re-enters the distal end of cannula 705 to form a distal loop 712. The electrode apparatus 700 has a cannula 705, an electrode wire 710 that forms a loop 712 at a distal end of the apparatus 700, a clasp 715 provided at a distal end of the cannula 705, and a handle portion 720 having a slider mechanism 725 and a release mechanism 730. The electrode apparatus 700 includes other features not shown in FIGS. 7A-7F, including, for example, a ground wire. FIG. 7A shows placement of the electrode apparatus 700 within a surgical site 255. In particular, the electrode wire 710 forms the loop 712, with the distal end of the electrode wire 710 being releasably held in the clasp 715. A proximal end of the electrode wire 710 is operably attached to the slider mechanism 725 within the handle portion 720. In some aspects, the connection between the electrode wire 710 and the slider mechanism 725 may be indicated through a slot 735 of the slider mechanism 725.

During use, the cannula 705 is placed adjacent to a tissue end 235, and the loop 712 formed by the electrode wire 710 is placed around the tissue end 235. A slider 740 of the slider mechanism 725 is configured to provide slack or tension to the electrode wire 710, allowing for tightening or loosening the loop 712, respectively. In FIG. 7B, the slider 740 is in a forward or distal position, providing slack to the electrode wire 710, as shown in FIG. 7A, to facilitate placement of the loop 712 around the tissue end 235.

FIG. 7C shows tensioning of the electrode wire 710, that is, tightening of the loop 712, via moving of the slider 740 in a proximal direction, as shown in FIG. 7D. The electrode wire 710 may be tightened after placement of the loop on the tissue end, e.g., after placement of a tissue graft 260 in the surgical site 255. The tensioning of the electrode wire 710 may be restricted, for example, to a pre-set limit based on the location of the connection between the electrode wire 710 and the slider mechanism 725. Once the electrode wire 710 is tightened around the tissue 235, electrical stimulation therapy may begin. The surgical site 255 may be substantially closed before, during, or after commencement of electrical stimulation therapy, with a small opening 265 remaining, through which the cannula 705 passes while electrical stimulation therapy continues. In other aspects, electrical stimulation therapy may begin once the surgical site 255 is closed. Upon completion of electrical stimulation therapy, the distal end of the electrode wire 710 may be disengaged from the clasp 715, as shown in FIG. 7E. The distal end of the electrode wire 710 may be disengaged from the clasp 715, e.g., by pressing a release button 745 of the release mechanism 730. Release of the connection between the electrode wire 710 and the clasp 715 may be confirmed visually through the slot 735 of the slider mechanism 725. For example, a portion of the electrode wire 710 may have indicia on a peripheral surface thereof, such that, when the electrode wire is retracted by a set amount, or length, after disengagement of the distal end from the clasp 715, the indicia is visible in the slot 735. The electrode wire 710 may then be retracted into the cannula 705 by moving slider mechanism 725 in the proximal direction, and the cannula 705 may be removed from the surgical site 255. By virtue of this embodiment, the electrode apparatus 700 can be removed from the surgical site 255, without damaging the tissue 235 or the tissue graft 260. It will be recognized that although a slider mechanism and release button 745 are described in this embodiment, any suitable actuator, e.g., button, knob, lever, switch, thumbwheel, etc., may be incorporated in handle portion 720 in order to achieve the functions described above.

The electrode apparatus 700 of the embodiment shown in FIGS. 7A-7F may limit an amount of compression that may be applied to the tissue 235, by, for example, setting a limit to the amount of slack or tension that may be provided to the electrode wire 710. The electrode apparatus 700 of this embodiment may also provide positive feedback of disengagement of the electrode wire 710, as a surgeon may confirm visually via the slot 235 of the slider mechanism 725, that the distal end of the electrode wire 710 has been disconnected from the clasp 715. This embodiment may also provide up to 360° of connection or conduction to the tissue 235. Further, minimal training may be required for installation and removal of the electrode apparatus 700. This embodiment may also provide for an electrode apparatus 700 that may be implanted during a surgical procedure, may remain in place after closure of a surgical site, e.g., while a patient is in recovery, to continue electrical stimulation therapy, and may be easily removed upon completion of the electrical stimulation therapy, without requiring additional surgical processes or resources.

Figures 8A, 8B, 9A, 9B, 9C, 9D, 9E, 9F:
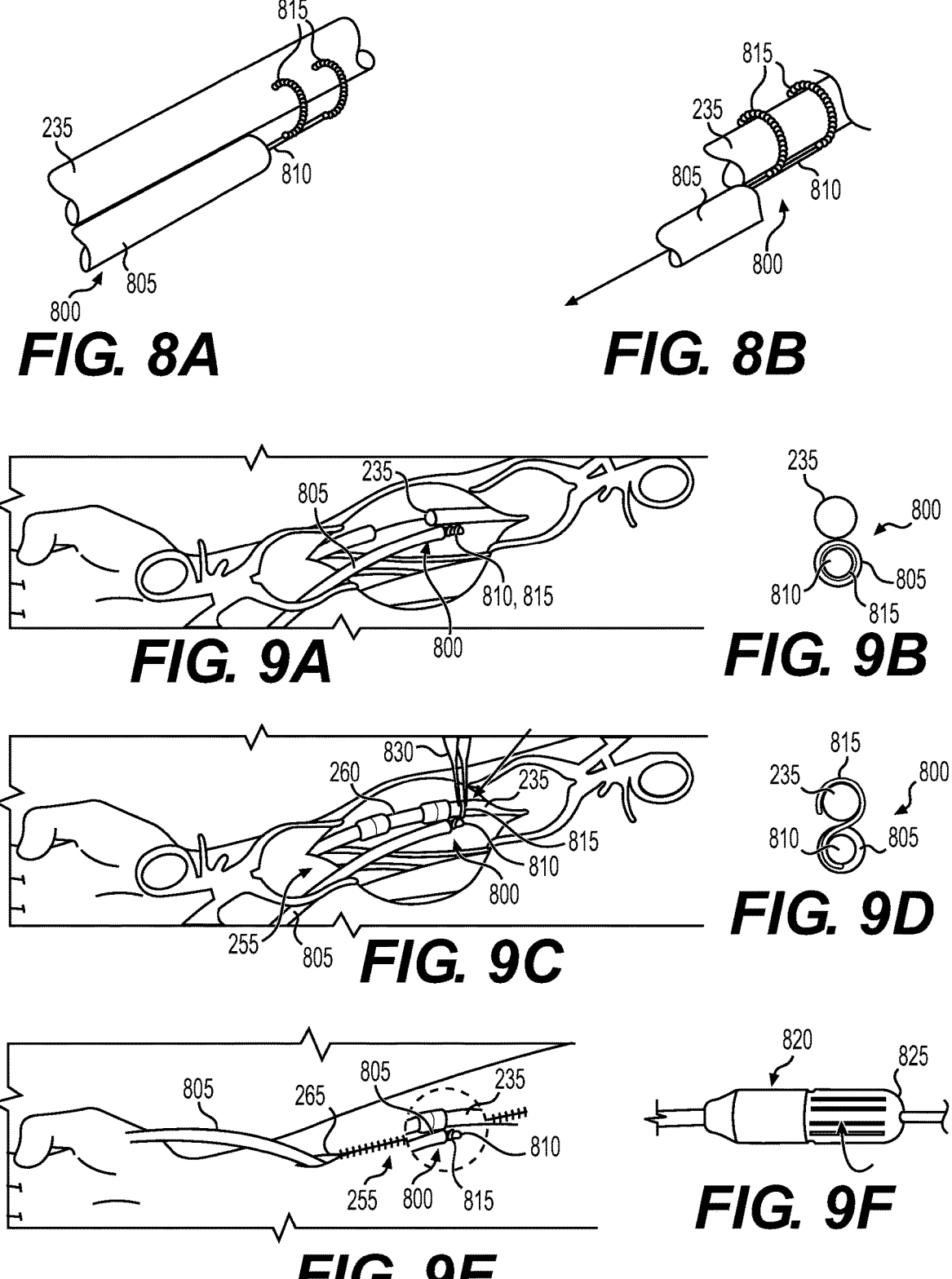
FIGS. 8A and 8B are schematic views of portions of an exemplary electrode apparatus during use, according to one or more embodiments.
FIGS. 9A-9F are schematic views of portions of the electrode apparatus shown in FIGS. 8A and 8B during use.

FIGS. 8A-9F show an electrode apparatus 800 having a coil-shaped electrode wire 810, according to another embodiment. The electrode apparatus 800 has a cannula 805, an electrode wire 810 with a flexible spring coil 815 at a distal end thereof, and a handle portion 820 with a rotatable knob 825. The electrode apparatus 800 includes other features not shown in FIGS. 8A-9F, including, for example, a ground wire. FIG. 8A shows the electrode wire 810 of the electrode apparatus 800, with the flexible spring coil 815 being wrapped around the electrode wire 810, formed from a semi-rigid core material, and the electrode wire 810 being wrapped around a tissue 235. A surgeon may manually wrap a free end of the electrode wire 810 around the tissue 235 during placement of the apparatus 800, as shown in FIG. 8B. Then, during removal of the apparatus 800, the electrode wire 810 may be rotated to unwind the soft spring coil 815 from the tissue 325, while retracting the electrode wire 810 into the cannula 805.

FIGS. 9A-9F show placement, securing, and removal of the electrode apparatus 800 shown in FIGS. 8A and 8B. In particular, FIG. 9A shows placement of the cannula 805 adjacent to an end of a transected tissue 235, which may occur before or after installation of a tissue graft 260. FIG. 9B shows a cross-sectional view of the cannula 805, the electrode wire, and the tissue 235, before the flexible spring coil 815 has been wrapped around the tissue 235. FIG. 9C shows wrapping of the electrode wire 810 around the tissue 235 using a tool 830, such as a forceps, and FIG. 9D shows a cross-sectional view of the cannula 805, the electrode wire 810, and the tissue 235, with the flexible spring coil 815 being wound onto the tissue 235. Although electrode wire 810 is shown in conjunction with a tissue graft 260 inserted between two portions of severed tissue 235, electrode wire 810 may be used in conjunction with two ends of severed tissue 235 rejoined without the use of a graft 260, or may be used with a tissue 235 that is not severed, since the flexible spring coil 815 may be wrapped around a peripheral surface of a tissue 235. If used in conjunction with severed tissue 235, the flexible spring coil 815 may be applied either before or after placement of a tissue graft 260, or reconnection with an end of severed tissue 235.

Once the spring coil 815 of the electrode wire 810 is secured around the tissue 235, electrical stimulation therapy may begin. Then, the surgical site 255 may be substantially closed before, during, or after commencement of electrical stimulation therapy, with a small opening 265 remaining, as shown in FIG. 9E, through which the cannula 805 passes while electrical stimulation therapy continues. In other aspects, electrical stimulation therapy may begin once the surgical site 255 is closed. Upon completion of electrical stimulation therapy, the electrode wire 810 may be disengaged from the tissue 235 by rotating the electrode wire 810 so that the spring coil 815 unwinds from the tissue 235, as shown in FIG. 9E. The electrode wire 810 may be rotated using the knob 825 on the handle portion 820, as shown in FIG. 9F. Then, the cannula 805 and the electrode wire 810 may be retracted or withdrawn through the small opening 265.

By virtue of the embodiment shown in FIGS. 8A-9F, an electrode apparatus 800 having a relatively simple installation procedure may be provided. The electrode apparatus 800 of this embodiment may provide up to 360° connection between the electrode wire 810 and the tissue 235. In addition, positive feedback of disengagement from the tissue 235 may be provided when the knob 825 stops rotating, indicating the coil 815 has been completely retracted into the cannula 805. This embodiment provides for another electrode apparatus 800 that may be implanted during a surgical procedure, may remain in place after closure of a surgical site, e.g., while a patient is in recovery, to continue electrical stimulation therapy, and may be easily removed upon completion of the electrical stimulation therapy, without requiring additional surgical processes or resources.

Figures 10, 11A, 11B, 11C, 11D, 11E, 11F:
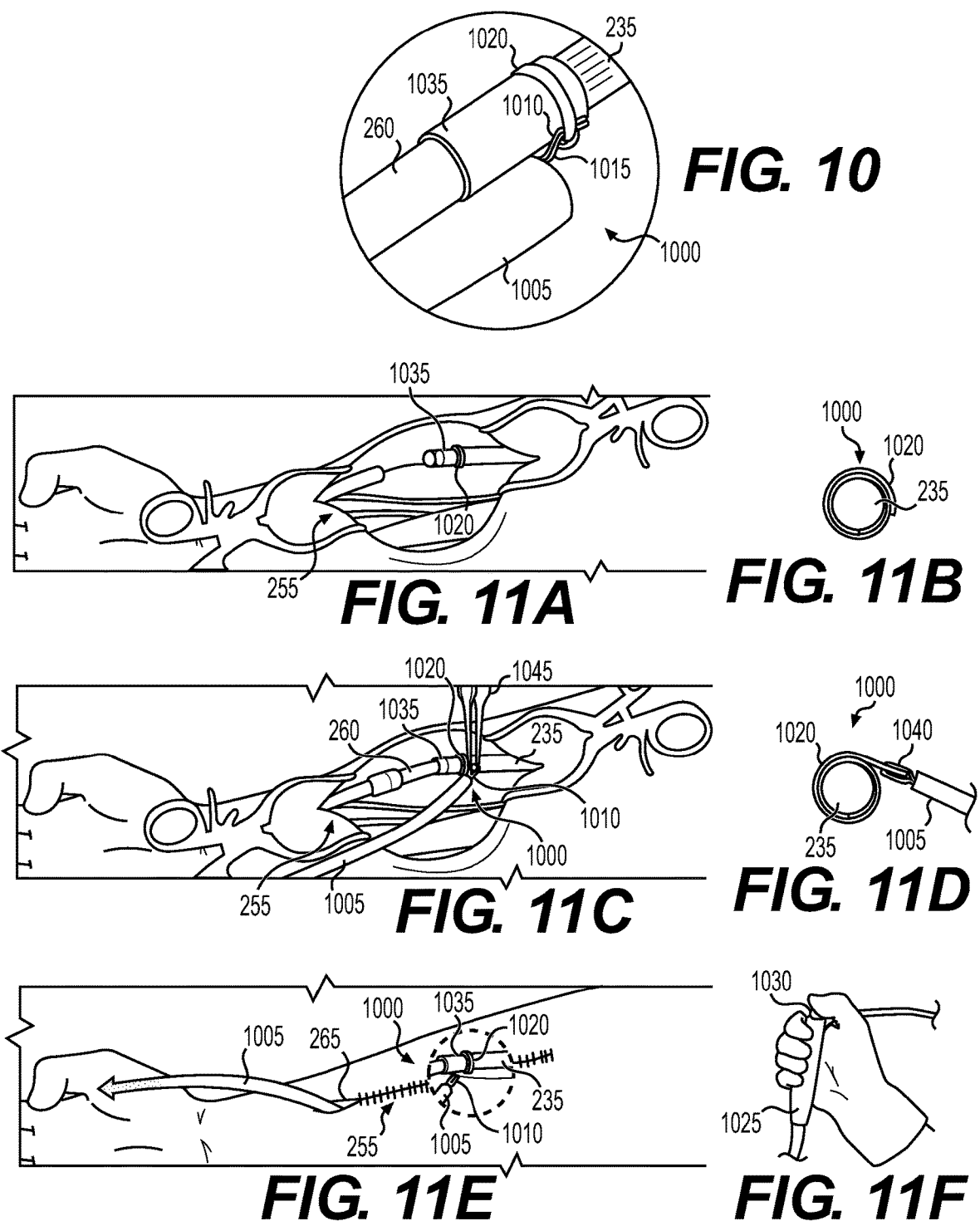
FIG. 10 is a schematic detail view of an exemplary electrode apparatus, according to one or more embodiments.
FIGS. 11A-11F are schematic views of portions of the electrode apparatus shown in FIG. 10 during use.

FIGS. 10 and 11A-11F show an electrode apparatus 1000 for use with a conductive ring 1020, according to another embodiment. The electrode apparatus 1000 has a cannula 1005, an electrode wire 1010, a ground wire 1015, a conductive ring 1020, a handle portion 1025 (FIG. 11F), and a release button 1030 (FIG. 11F) provided on the handle portion 1025. The electrode apparatus 1000 may be used with a sleeve 1035. In particular, FIG. 10 shows a detail view of the sleeve 1035 with the conductive ring 1020 installed thereon. A cannula 1005 is provided adjacent to the sleeve 1035, and the electrode wire 1010 and the ground wire 1015 extend through a distal end of the cannula 1005 and are connected, for example, by a tab 1040, shown in FIG. 11D, to the conductive ring 1020. The conductive ring 1020 may be formed of an electrically conductive material, which may also be a biologically compatible material, or an absorbable conductive compound. In particular, the conductive ring 1020 may be formed from a bioresorbable conductive wire, such as a wire formed from an electron-beam evaporated magnesium layer on a surface of a polymer fiber, and insulated with an extrusion coated polymer sheath (e.g., a wire formed of a bioresorbable poly(desanino tyrosyl-tryosine ethyl ester carbonate) or poly(DTE carbonate) core fiber, coated with magnesium, and extrusion coated with bioresorbable poly(caprolactane) (PCL)) (as discussed in Palmroth et al., "Bioresorbable Conductive Wire and Minimal Metal Content," ACS Biomater. Sci. Eng., 2019, Vol. 5(5), pp. 1134-1140, or such as those discussed in Li et al., "Processing Techniques for Bioresorbable Nanoparticles in Fabricating Flexible Conductive Interconnects," Materials, 2018, Vol. 11, pp. 1-9.

FIGS. 11A-11F are schematic views of the electrode apparatus 1000 and conductive ring 1020 shown in FIG. 10. FIG. 11A shows placement of the sleeve 1035 including the conductive ring 1020 on an end of a transected tissue 235 within a surgical site 255. The sleeve 1035 into which conductive ring 1020 is incorporated may be a wrap or other suitable covering for a tissue. For example, sleeve 1035 may be an Axogen Nerve Connector® or Axogen Nerve Protector®, and may be in the form of a sheet that is wrapped around tissue 235, or pre-rolled and fit over a severed end of a tissue 235. In such an embodiment, conductive ring 1020 may be incorporated on a surface of, or may extend through or along a side of the Nerve Connector®, Nerve Protector®, or other wrap or covering, and tab 1040 may also be included and configured to electrically connect the electrode wire 1010 with the conductive ring 1020. FIG. 11B shows a cross-sectional view of a tissue 235 and the conductive ring 1020. FIG. 11C shows placement of the cannula 1005 with the electrode wire 1010 adjacent to the tissue 235 and the sleeve 1035 with the conductive ring 1020 around the tissue 235. A tool 1045 may be used to attach the electrode wire 1010 and the ground wire 1015 to the conductive ring 1020. FIG. 11D shows a cross-sectional view of the tissue 235 with the conductive ring 1020 and the tab 1040, connecting the conductive ring 1020 to the electrode wire 1010 and the ground wire 1015 at the distal end of the cannula 1005. Although electrode wire 1010 is shown in conjunction with a tissue graft 260 inserted between two portions of severed tissue 235, electrode wire 1010 may be used in conjunction with two ends of severed tissue 235 rejoined without the use of a graft 260, or may be used with a tissue 235 that is not severed, in a case in which a sleeve 1035 with a conductive ring 1020 is wrapped around a tissue 235.

Once the wires are attached to the conductive ring 1020, electrical stimulation therapy may begin. Then, the surgical site 255 may be substantially closed before, during, or after commencement of electrical stimulation therapy, with a small opening 265 remaining through which the cannula 1005 passes while electrical stimulation therapy continues. In other aspects, electrical stimulation therapy may begin once the surgical site 255 is closed. Upon completion of electrical stimulation therapy, the electrode wire 1010 and the ground wire 1015 are detached from the conductive ring 1020. FIG. 11E shows the detachment of the wires from the conductive ring 1020. FIG. 11F shows pressing of the release button 1030 on the handle portion 1025, for release of the electrode wire 1010 and the ground wire 1015 from the conductive ring 1020. In particular, pushing the release button 1030 on the handle portion 1025 may release the clasping force of 1040 by extending the electrode wire 1010 out of the cannula 1005, allowing the electrode wire 1010 to separate. Pushing or pressing the release button 1030 until a click or other audible or tactile indication is provided, may confirm that the release button 1030 is fully depressed and may confirm that the electrode wire 1010 is released from the conductive ring 1020. Once the wires are detached from the conductive ring 1020, the cannula 1005 and the wires can be retracted from the surgical site 255, and the small opening 265 can be closed.

By virtue of the embodiment shown in FIGS. 10 and 11A-11F, up to 360° connection of the conductive ring 1020 around the tissue 235 is ensured. In addition, no wires or connections would be expressed, or extended beyond the distal end of the cannula 1005, on the exterior of the electrode apparatus 1000 prior to removal of the electrode apparatus 1000. This embodiment provides for another electrode apparatus 1000 that may be implanted during a surgical procedure, may remain in place after closure of a surgical site, e.g., while a patient is in recovery, to continue electrical stimulation therapy, and may be easily removed upon completion of the electrical stimulation therapy, without requiring additional surgical processes or resources.

FIGS. 12, 13, and 14A-14B show an electrode apparatus 1200 having a dissolvable seam 1225, according to another embodiment. The electrode apparatus 1200 includes a cannula 1205, an electrode wire 1210, a ground wire 1215, a conductive loop 1220 attachable to the electrode wire 1210 and the ground wire, and a dissolvable seam 1225 attached to a sleeve 1230. As described above, the sleeve 1230 into which conductive loop 1220 and dissolvable seam 1225 are incorporated may be an Axogen Nerve Connector® or Axogen Nerve Protector®, and may be in the form of a sheet that is wrapped around tissue 235, or pre-rolled and fit over a severed end of a tissue 235. The electrode wire 1210 and the ground wire 1215 may extend beyond a distal end of the cannula 1205, or may be extended beyond cannula 1205, and may be attached to the conductive loop 1220, as described in more detail with respect to FIGS. 14A and 14B. FIG. 13 shows a cross-sectional view of the tissue 235, the conductive loop 1220, and electrode wire 1210, the ground wire 1215, and the dissolvable seam 1225. The dissolvable seam 1225 may be positioned at a location that is substantially opposite to a location at which the electrode wire 1210 and the ground wire 1215 are attached to the conductive loop 1220, as shown. The dissolvable seam 1225 may, however, be provided at other locations on the conductive loop 1220. The dissolvable seam 1225 may be formed of, for example, BioGlue® (available from Cryolife, Inc.), chitosan, hyaluronic acid, modified hyaluronic acid, and/or polyvinyl alcohol. A material used to form the seam 1225 may be chosen based on a rate of dissolution of the material, which may be matched to a duration of therapy needed as well as time needed for placement of the device within a surgical site, or other procedures. The seam 1225 may dissolve, for example, after a period of time in a range of about 1 minute to about 60 minutes. In addition, an opening 1235 is provided in a portion of the conductive loop 1220, as shown in FIG. 13. As discussed in more detail below, the opening 1235 is configured to receive a portion of the electrode wire 1210 and a portion of the ground wire 1215.

FIGS. 14A and 14B are detail schematic side views of a portion of the conductive loop 1220, including the opening 1235, the cannula 1205, the electrode wire 1210, and the ground wire 1215. In particular, FIG. 14A shows the electrode wire 1210 and the ground wire 1215 extending beyond a distal end of the cannula 1205 towards the opening 1235 of the conductive loop 1220, with the arrow indicating a direction of insertion of the wires into the opening 1235 of the conductive loop 1220. FIG. 14B shows the ends of the electrode wire 1210 and the ground wire 1215 being snap fit onto the opening 1235 of the conductive loop 1220. The distal tips of the electrode wire 1210 and the ground wire 1215 may be shaped so as to hook into the opening 1235 of the conductive loop 1220. Other suitable connection mechanisms may be used instead of the snap-fit connection shown in FIGS. 14A, 14B.

In this example, the electrode wire 1210 and the ground wire 1215 may each have a tapered, arrowhead-type distal tip that is configured to be snap fit into the opening 1235 in the conductive loop 1220. Once the electrode wire 1210 and the ground wire 1215 are attached to the conductive loop 1220, electrical stimulation therapy may begin. The surgical site 255 may be substantially closed before, during, or after commencement of electrical stimulation therapy, with a small opening 265 remaining, through which the cannula 1205 passes while electrical stimulation therapy continues. In other aspects, electrical stimulation therapy may begin once the surgical site 255 is closed. Upon completion of electrical stimulation therapy, and once the seam 1225 has dissolved, the conductive loop 1220 may be disengaged from the tissue 235. Then, the cannula 1205, the electrode wire 1210, the ground wire 1215, and the conductive loop 1220 are retracted or withdrawn through the small opening 265.

Figures 15A, 15B, 15C, 15D, 15E:
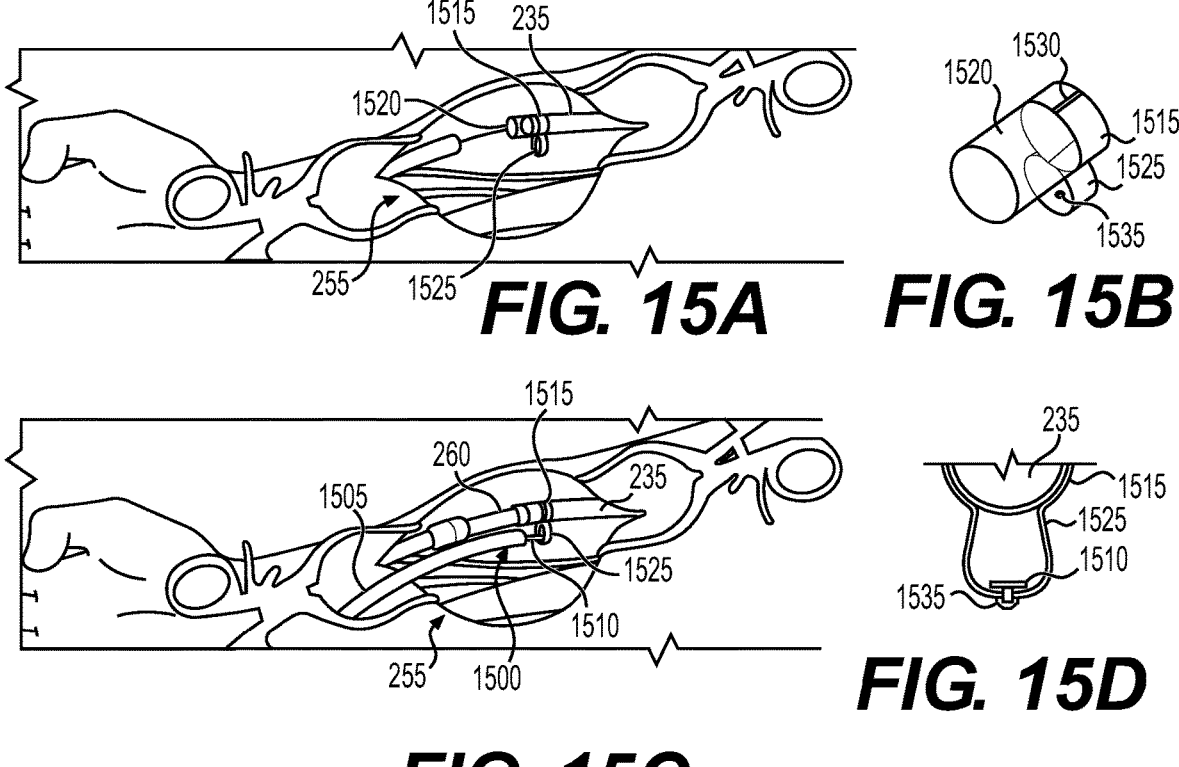
FIGS. 15A-15E are schematic views of portions of yet another exemplary electrode apparatus during use, according to one or more embodiments.

FIGS. 15A-15E are schematic views of an electrode apparatus 1500 according to another embodiment. The electrode apparatus 1500 has a cannula 1505, an electrode wire 1510, and a conductive ring 1515, similar to the conductive loop 1220 shown in FIGS. 12-14B, provided on a sleeve 1520. The conductive ring 1515 has a conductive loop portion 1525, shown in FIGS. 15A-15E, for attachment of the electrode wire 1510 upon placement of the cannula 1505 at a surgical site 255, and a dissolvable seam 1530. FIG. 15A shows placement of the conductive ring 1515 and a sleeve 1520, which may be integrated with the conductive ring 1515, on a tissue 235. FIG. 15B shows the dissolvable seam 1530 on the conductive ring 1515, and an opening 1535 in the conductive loop portion 1525 of the conductive ring 1515. The seam 1530 may be formed from a dissolvable material, such as BioGlue® (available from Cryolife, Inc.), chitosan, hyaluronic acid, modified hyaluronic acid, and/or polyvinyl alcohol. A material used to form the seam 1530 may be chosen based on a rate of dissolution of the material, which may be matched to a duration of therapy needed as well as time needed for placement of the device within a surgical site, or other procedures. The seam 1530 may dissolve, for example, after a period of time in a range of about 1 minute to about 60 minutes. FIG. 15C shows placement of the electrode apparatus 1500 into the surgical site 255, with the cannula 1505 being placed adjacent to the tissue 235, and the electrode wire 1510 extending through the cannula 1505, beyond a distal end, and being attached to the conductive loop portion 1525 of the conductive ring 1515. FIG. 15D shows a detail side view of the electrode wire 1510 attached to the conductive loop portion 1525 of the conductive ring 1515 through the opening 1535. In this example, the electrode wire 1510 may have a tapered, arrowhead-type distal tip that is configured to be snap fit into the opening 1535 in the conductive loop portion 1525. Once the electrode wire 1510 is attached to the conductive ring 1515, electrical stimulation therapy may begin. Then, the surgical site 255 may be substantially closed before, during, or after commencement of electrical stimulation therapy, with a small opening 265 remaining, through which the cannula 1505 passes while electrical stimulation therapy continues. In other aspects, electrical stimulation therapy may begin once the surgical site 255 is closed. Upon completion of electrical stimulation therapy, and once the seam 1530 has dissolved, the conductive ring 1515 may be disengaged from the tissue 235, as shown in FIG. 15E. Then, the cannula 1505, the electrode wire 1510, and the conductive ring 1515 are retracted or withdrawn through the small opening 265. The seam may dissolve, for example, after a period of time in a range of about 1 minute to about 60 minutes.

By virtue of the embodiments shown in FIGS. 12-15E, which incorporate use of a sleeve and a dissolvable seam, it is possible to eliminate an additional step of installing an electrode wire separately from a sleeve, rather the electrode wire and the ground wire can be attached to a conductive loop or a conductive ring when placing the electrode apparatus in a surgical site. In addition, the electrode apparatus 1200 and the electrode apparatus 1500 may be disengaged from a tissue upon dissolving of the seam, and therefore may not require action on the part of a surgeon to disengage the electrode wire from the tissue. These embodiments may also provide for up to 360° of conduction to the tissue 235 by use of the conductive loop 1220 and/or the conductive ring 1515. Further, minimal training may be required of surgeons for installation of the electrode apparatus of these embodiments. Further, these embodiments may provide for another electrode apparatus that may be implanted during a surgical procedure, may remain in place after closure of a surgical site, e.g., while a patient is in recovery, to continue electrical stimulation therapy, and may be easily removed upon completion of the electrical stimulation therapy, without requiring additional surgical processes or resources.

Figures 16A, 16B, 16C, 16D, 16E, 16F, 16G, 16H:
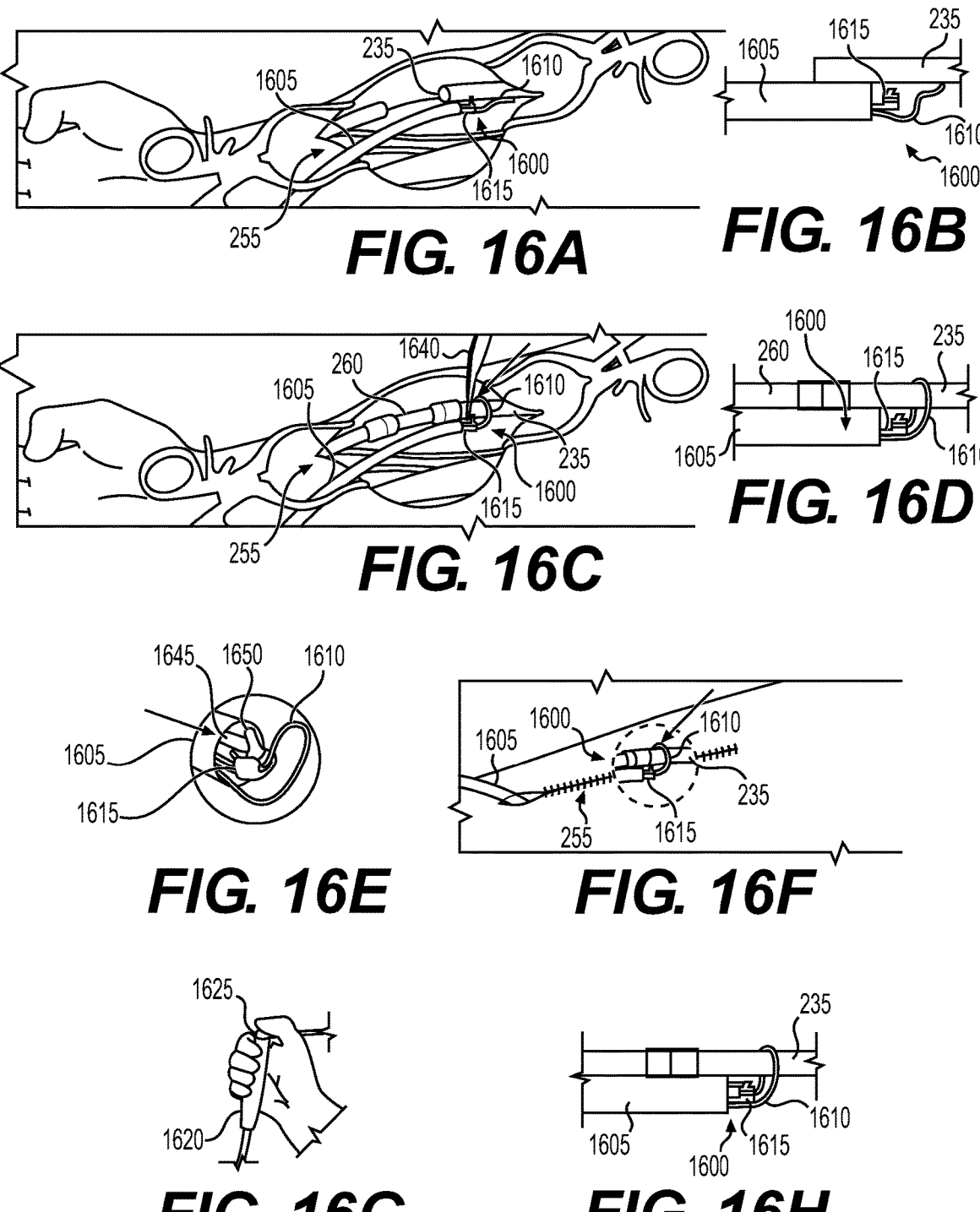
FIGS. 16A-16H are schematic views of portions of another exemplary electrode apparatus during use, according to one or more embodiments.

FIGS. 16A-17B show an electrode apparatus 1600 according to another embodiment. The electrode apparatus 1600 has a cannula 1605, an electrode wire 1610, a releasable cinch mechanism 1615 that operates similar to a zip-tie, a handle portion 1620, and a release mechanism 1625 provided on the handle portion 1620. The electrode apparatus 1600 may include other features not shown in FIGS. 16A-16H, including, for example, a ground wire. The electrode wire 1610 and the cinch mechanism 1615 may be extendable beyond a distal end of the cannula 1605. In particular, FIG. 16A shows placement of the cannula 1605 adjacent to a tissue 235, and FIG. 16B shows a side detail view of the electrode wire 1610 and the cinch mechanism 1615 extending beyond the distal end of the cannula 1605. FIG. 16C shows wrapping of the electrode wire 1610 around the tissue 235, following placement of a tissue graft 260. The electrode wire 1610 may be wrapped using a tool 1630, such as a forceps. The electrode wire 1610 may alternatively be wound around the tissue 235 prior to placement of a tissue graft 260. And, although electrode wire 1610 is shown in conjunction with a tissue graft 260 inserted between two portions of severed tissue 235, electrode wire 1610 may be used in conjunction with two ends of severed tissue 235 rejoined without the use of a graft 260, or may be used with a tissue 235 that is not severed, since the electrode wire 1610 may be wrapped around a peripheral surface of a tissue 235. If used in conjunction with severed tissue 235, the electrode wire 1610 may be applied either before or after placement of a tissue graft 260, or reconnection with an end of severed tissue 235. In either case, a free end of the electrode wire 1610 is wrapped around the tissue 235 and inserted into the cinch mechanism 1615. The electrode wire 1610 can be pulled through the cinch mechanism 1615 using tool 1630 until a desired tightness of the wrapping of the electrode wire 1610 around the tissue 235 is achieved. FIG. 16D shows the electrode wire 1610 pulled through the cinch mechanism 1615.

Once the electrode wire 1610 is securely wrapped around the tissue 235, electrical stimulation therapy may begin. Then, the surgical site 255 may be substantially closed before, during, or after commencement of electrical stimulation therapy, with a small opening 265 remaining, through which the cannula 1605 passes while electrical stimulation therapy continues. In other aspects, electrical stimulation therapy may begin once the surgical site 255 is closed. Upon completion of electrical stimulation therapy, the electrode wire 1610 is disengaged from the tissue 235. In particular, as shown in FIG. 16E, a pushrod 1645, which is mechanically connected to and actuated by the release mechanism 1625, pushes a release tab 1650 of cinching mechanism 1615, which moves, e.g. rotates, to thereby release the free end of the electrode wire 1610 from the cinch mechanism 1615. FIG. 16F shows the release of electrode wire 1620, and FIG. 16G shows pressing of the release mechanism 1625 (here, a button) on the handle portion 1620. Although release mechanism 1625 is depicted as a button, it is understood that any suitable mechanism, e.g., a lever, a switch, a slider, a thumbwheel, etc., may be incorporated in handle portion 1620 to control release of electrode wire 1610. FIG. 16H shows a detail side view of the release electrode wire 1610. Then, the cannula 1605 and the electrode wire 1610 are retracted withdrawn through the small opening 265, which can be closed following removal.

FIGS. 17A and 17B are schematic detail views of the releasable cinch mechanism 1615 at a distal end of the electrode apparatus 1600 shown in FIGS. 16A-16H. In particular, FIG. 17A shows wing portions 1655a, 1655b of the cinch mechanism 1615 in a cinching position. In this example, the wing portions 1655a, 1655b are configured to rotate about axes A and B, so that in the cinching position, ridges 1660 provided on a surface of each wing portion 1655a and 1655b are positioned near each other. In this position, an electrode wire 1610 inserted into the cinch mechanism 1615 is gripped by the ridges 1660 and retained between the wing portions 1655a, 1655b. When the release tab 1650 is pushed in the direction of the arrow shown in FIG. 16E, the wing portions 1655a, 1655b rotate about axes A, B, respectively to an open position, shown in FIG. 17B, such that smooth surfaces 1665 thereof are oriented towards the electrode wire 1610, and the electrode wire 1610 inserted between the wing portions 1655a, 1655b is no longer gripped by the ridges 1660, and may be pulled out from the cinch mechanism 1615.

The electrode apparatus 1600 of the embodiment shown in FIGS. 16A-17B provides for a secure mechanical connection between the electrode apparatus 1600 and the tissue 235, with minimal surgical techniques needed for installation. The electrode apparatus 1600 of this embodiment may also be placed before or after placement of a tissue graft 260 at the surgical site 255, if a tissue graft 260 is used. This embodiment also provides for up to 360° of connection or conduction to the tissue 235. This embodiment also provides for an electrode apparatus 1600 that may be implanted during a surgical procedure, may remain in place after closure of a surgical site, e.g., while a patient is in recovery, to continue electrical stimulation therapy, and may be easily removed upon completion of the electrical stimulation therapy, without requiring additional surgical processes or resources.

FIGS. 18A-18H show an electrode apparatus 1800 including a hook 1815 and a wire loop 1812, according to another embodiment. The electrode apparatus 1800 has a cannula 1805, an electrode wire 1810 having a loop 1812 at a distal end thereof, and a hook 1815 at a distal end of the cannula 1805. In particular, FIG. 18A shows the hook 1815 and the looped electrode wire 1810 in an extended or exposed position. In this embodiment, the extended or exposed position of the hook 1815 and the looped electrode wire 1810 is the starting position for a procedure in which the electrode wire 1810 is to be placed around a nerve 235, however, the electrode wire 1810 and the hook 1835 may be retracted within the cannula during placement of the electrode apparatus 1800 in the surgical site 255, and then may be extended distally to the starting position, once the apparatus 1800 is in place. The electrode wire 1810 extends distally of a distal end of the cannula 1805, and the looped end of the electrode wire 1810 may be loose or slack. The hook 1815 may also extend distally of the distal end of the cannula 1805.

FIG. 18B shows a handle portion 1820 of the electrode apparatus 1800 in the starting position. In this embodiment, the handle portion 1820 of the electrode apparatus has an inlet 1825, a wire retraction spring 1830 operatively connected to the electrode wire 1810 and provided within the handle portion 1820, a trigger 1835 for extending and retracting the hook 1815, a thumbwheel 1840 for controlling slackening and tightening of the looped electrode wire 1810, an indicator window 1845 used to indicate whether the electrode wire 1810 is disconnected from the hook 1815, and an outlet 1850 through which the cannula 1805 extends distally to the handle portion 1820. The wire retraction spring 1830 applies a spring load to retract the wire 1810 in a proximal direction. The indicator window 1845 has a flag 1855 configured to be positioned within the indicator window 1845 when the wire 1810 is retracted, as shown in FIG. 18G, and that is positioned outside of the indicator window 1845, or hidden, when the wire 1810 is extended, as shown in FIGS. 18B and 18E (or vice versa). Although a flag 1855 is described as being present or absent in order to indicate the position of wire 1810, any suitable indicator may be used. For example, different colors may be shown in the indicator window 1845 to convey the position of wire 1810 to a viewer. Inclusion of indicator window 1845 may allow a user to confirm retraction of the electrode wire 1810 prior to retraction of the electrode apparatus 1800 from the surgical site 255.

FIG. 18C shows the looped electrode wire 1810 being wrapped around a tissue 235, and being looped onto the hook 1815, using a tool 1860, such as a forceps. That is, a surgeon may use the tool 1860 to manipulate the distal portion of the electrode wire 1810, or the loop 1812, so that the loop 1812 wraps around the tissue 235 and catches onto the hook 1815. FIG. 18D shows the hook 1815 and the loop 1812 in a retracted position, after the loop 1812 has been wrapped around the tissue 235. The arrow in FIG. 18D indicates the direction in which the hook 1815 retracts into the cannula 1805, bringing a portion of the looped electrode wire 1810 into the cannula 1805 as well. FIG. 18E shows a direction of rotation of a thumbwheel 1840 when retracting the electrode wire 1810 and thereby tightening the loop 1812 around the tissue 235. The thumbwheel 1840 may operate through use of a friction wheel (not shown), which contacts the electrode wire 1840 within the handle portion 1820, such that when the thumbwheel 1840 rotates, the electrode wire 1810 translates in a direction so as to extend the electrode wire 1810 in a distal direction (which loosens the loop 1812), or to retract the electrode wire 1810 in a proximal direction (to tighten the loop 1812 or, when the loop 1812 is disengaged from the hook 1815, to retract the electrode wire 1810). When the hook 1815 and the electrode wire 1810 are in the positions shown in FIG. 18D, electrical stimulation therapy may be performed while the electrode wire 1810 is wrapped around the tissue 235. Then, when electrical stimulation therapy is complete, the hook 1815 may be exposed or extended out of the distal end of the cannula 1805, and the looped electrode wire 1810 may be loosened, as shown in FIG. 18F. The arrow in FIG. 18F shows a direction in which the hook 1815 extends, to allow for release of the loop 1812. That is, as the hook 1815 rotates or extends out of the distal end of the cannula 1805, an end of the hook 1815 extends outward and the loop 1812 of the electrode wire 1810 slides off the hook 1815.

FIG. 18G shows a rotation direction of the thumbwheel 1840 and compression of the trigger 1835 to extend the hook 1815 and the loop 1812 to the positions shown in FIG. 18F. More specifically, by pressing the trigger 1835 in the direction of the arrow shown in FIG. 18G, the hook 1815 extends and/or rotates out of the distal end of the cannula 1805. And, by rotating the thumbwheel 1840 in the direction of the arrow shown in FIG. 18G, the distal end of the electrode wire 1810 becomes relatively slack or loose, allowing the loop 1812 of the electrode wire 1810 to slip off the extended hook 1815. Finally, FIG. 18H shows retraction of the electrode wire 1810 into the cannula 1805. The arrow shown in FIG. 18H indicates a direction in which the electrode wire 1810 retracts into the cannula 1805, upon turning of the thumbwheel 1840 in a direction shown by the arrow in FIG. 18E. According to this embodiment, one or both of the looped electrode wire 1810 or hook 1815 may be retracted into the cannula 1805 before removal of the cannula 1805 from a surgical site, or, one or both of the looped electrode wire 1810 or hook 1815 may remain extended distal to the end of cannula 1805 during removal of the cannula 1805 from the surgical site.

FIGS. 19A-19I are schematic views of an electrode apparatus 1900 according to another embodiment. The electrode apparatus 1900 has a cannula 1905, an electrode wire 1910 having a loop 1912, and a hook 1915 extendable and retractable into a distal end of the cannula 1905. The electrode apparatus 1900 also has a handle portion 1920, an inlet 1925, a trigger 1930 for extending and retracting the hook 1915, a thumbwheel 1935 for controlling slackening and tightening of the electrode wire 1910, including the loop 1912, an indicator window 1940 in which a flag 1945 displays depending on whether or not the electrode wire 1910 is disconnected from the hook 1915, and an outlet 1950 through which the cannula 1905 extends distally from the handle portion 1920.

In particular, FIG. 19A shows the electrode wire 1910 and the hook 1915 in a retracted position. In this embodiment, the retracted position of the hook 1915 and the electrode wire 1910 is the starting position for a start of a surgical procedure. FIG. 19B shows elements of a handle portion 1920 of the electrode apparatus 1900 including the inlet 1925, the trigger 1930 for extending and retracting the hook 1915, the thumbwheel 1935 for controlling slackening and tightening of the electrode wire 1910, the indicator window 1940, and the outlet 1950 through which the cannula 1905 extends distally relative to the handle portion 1920. The flag 1945 is displayed in the indicator window 1940 when the wire 1910 is retracted, as shown in FIG. 19B, and is positioned outside of the indicator window 1940 (that is, not displayed in the indicator window 1940) when the wire 1910 is extended, as shown in FIG. 19D. As described above, although a flag 1945 is described as being present or absent in indicator window 1940 in order to indicate the position of wire 1910, any suitable indicator may be used. For example, different colors may be shown in the indicator window 1940 to convey the position of wire 1910 to a viewer. Inclusion of indicator window 1940 may allow a user to confirm the position of the electrode wire 1910 during a procedure.

Figures 19E, 19F, 19G, 19H, 19I, 20A, 20B, 20C:
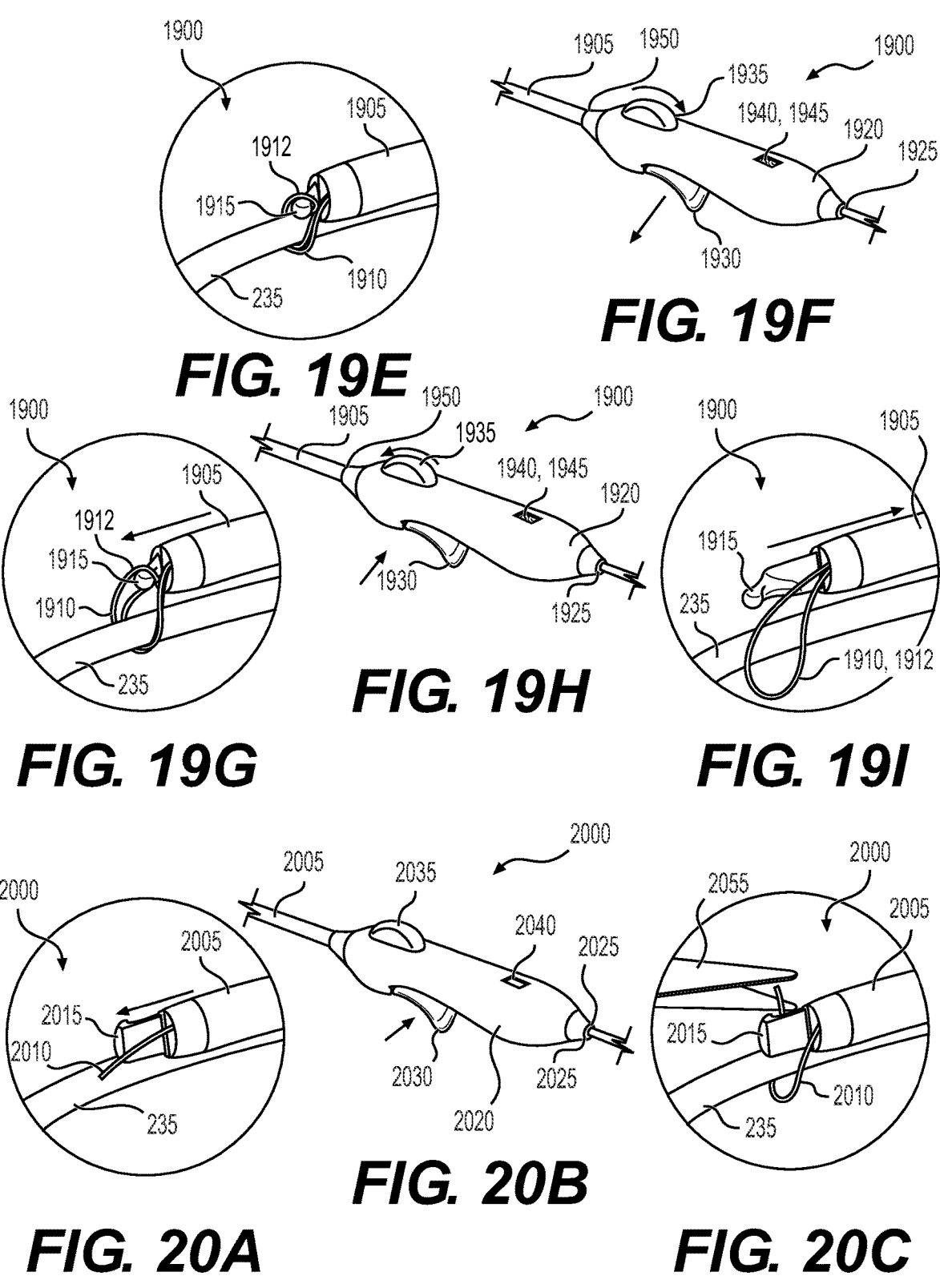

FIG. 19C shows the electrode wire 1910 and the hook 1915 in an extended position, with the loop 1912 of the electrode wire 1910 being wrapped around a tissue 235 and onto the hook 1915, using a tool 1955, such as a forceps. That is, a surgeon may use the tool 1955 to manipulate the distal region of the electrode wire 1910, or the loop 1912, so that the loop 1912 wraps around the tissue 235 and catches onto the hook 1915. FIG. 19D shows a rotation direction of the thumbwheel 1935 for extending or loosening the electrode wire 1910, and a pulling or compression of the trigger 1930 to extend the hook 1915 so as to extend out of the distal end of the cannula 1905. FIG. 19E shows the hook 1915 in a retracted state, after the electrode wire 1910 has been wrapped around the tissue 235 and the hook 1915. FIG. 19F shows a rotation direction of the thumbwheel 1935 and a release direction of the trigger 1930. Rotating the thumbwheel 1935 tightens the loop 1912 formed by the electrode wire 1910, and release of the trigger 1930 retracts the hook 1915 into the distal end of the cannula 1905.

Once the hook 1915 and the electrode wire 1910 are in the state shown in FIG. 19E, electrical stimulation therapy may be performed. Then, upon completion of the electrical stimulation therapy, the hook 1915 may be extended by compressing the trigger 1930, as shown in FIG. 19H, for release of the wire 1910. To ensure the loop 1912 of the electrode wire 1910 is released from the hook 1915, the thumbwheel 1935 may be rotated in the direction shown in FIG. 19H. FIG. 19I shows the electrode wire 1910 having been released from the hook 1915 and unwrapped from the tissue 235, and ready for retraction and removal from the surgical site 255. According to this embodiment, the electrode wire 1910 and the hook 1915 remain extended during removal of the cannula 1905. In other aspects, however, one or both of electrode wire 1910 and the hook 1915 may be retracted into cannula 1905 during removal.

Figure 20D:
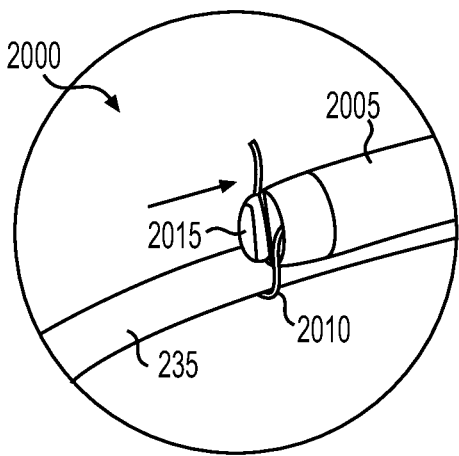
Figure 20E:
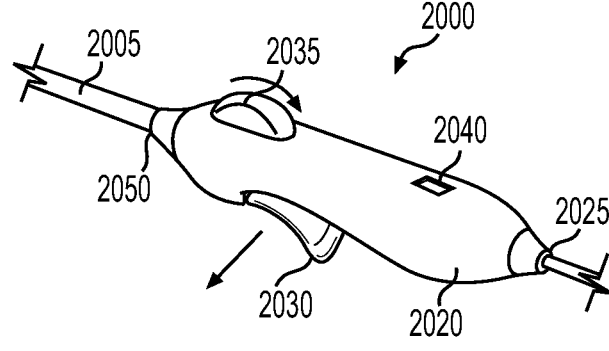
Figure 20F:
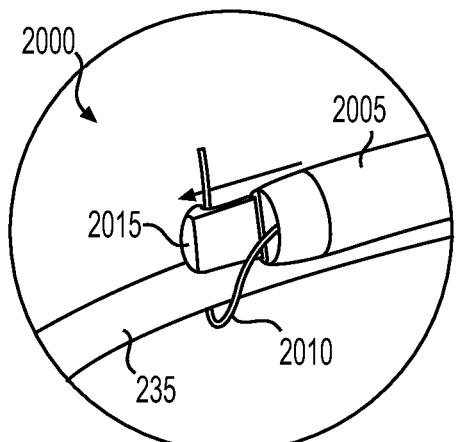
Figure 20G:
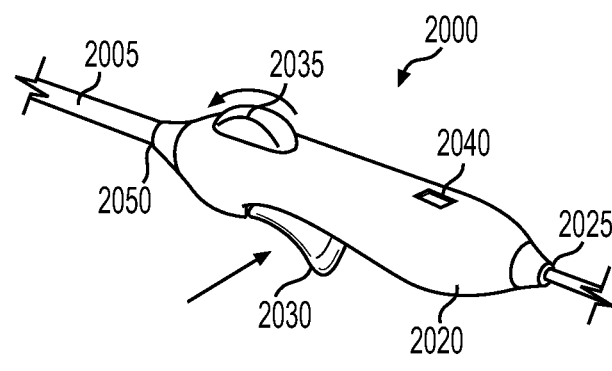

FIGS. 20A-20K are schematic views of an electrode apparatus 2000 according to another embodiment. The electrode apparatus 2000 has a cannula 2005, an electrode wire 2010, and a hook 2015 at a distal end of the cannula 2005. The electrode apparatus 2000 also has a handle portion 2020, an inlet 2025, a trigger 2030 for extending and retracting the hook 2015, a thumbwheel 2035 for controlling slackening and tightening of the looped electrode wire 2010, an indicator window 2040 in which a flag 2045 displays depending on whether or not the electrode wire 2010 is disconnected from the hook 2015, and an outlet 2050 through which the cannula 2005 extends distally from the handle portion 2020. In particular, FIG. 20A shows a direction in which hook 2015 extends outward from a distal end of the cannula 2005, upon squeezing of the trigger 2030 in a direction of the arrow shown in FIG. 20B. FIG. 20C shows wrapping of the electrode wire 2010 around a tissue 235 and around the extended hook 2015, which may be performed by a surgeon using a tool 2055, such as a forceps. Once the electrode wire 2010 is wrapped around the tissue 235 and the hook 2015, the hook 2015 may be retracted and the electrode wire 2010 may be tightened, as shown in FIG. 20D. That is, the hook 2015 may be retracted into the distal end of the cannula 2005 in the direction of the arrow shown in FIG. 20D. FIG. 20E shows a rotation direction of the thumbwheel 2035 to retract the electrode wire 2010, and release of the trigger 2030 to retract the hook 2015. Once the electrode wire 2010 and the hook 2015 are in the wrapped and retracted positions shown in FIG. 20D, electrical stimulation therapy may be performed. Then, upon completion of electrical stimulation therapy, the hook 2015 may be extended outward from the distal end of the cannula 2005 by compressing the trigger 2030, and the electrode wire 2010 may be loosened, as shown in FIG. 20F. FIG. 20G shows a compression direction of the trigger 2030 to extend the hook 2015, and the direction of rotation of the thumbwheel 2035 to loosen the electrode wire 2010.

Figure 20H:
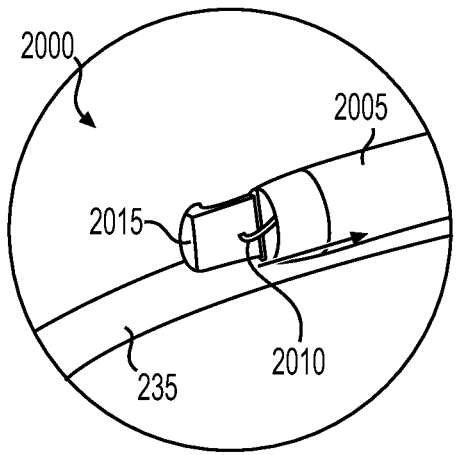
Figure 20I:
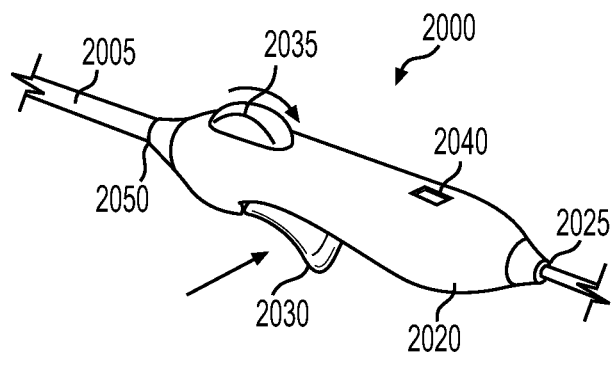
Figures 20J, 20K, 21A, 21B, 21C, 22A, 22B, 22C:
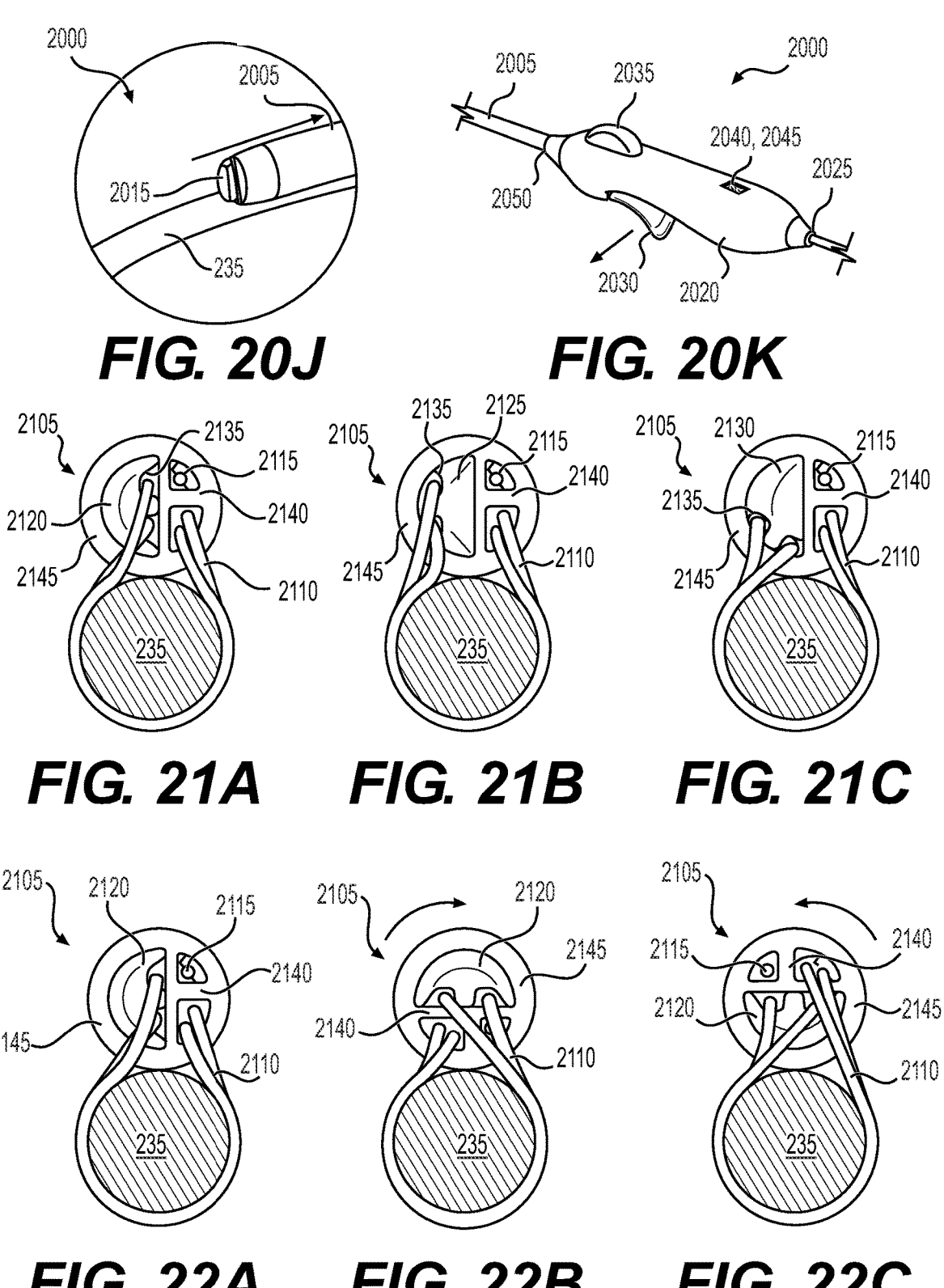

In this embodiment, if a user tries to rotate the thumbwheel 2035 and retract the wire 2010 without releasing the trigger 2030 (i.e., retracting hook 2015 back into cannula 2005), rotation of the thumbwheel 2035 would not retract the electrode wire 2010. This may prevent tightening of the electrode wire 2010 around the tissue 235, and ensures that the electrode wire 2010 may only be retracted upon release of the trigger 2030, and thus removal of electrode wire 2010 from around tissue 235. FIG. 20H shows retraction of the released electrode wire 2010 into the distal end of the cannula 2005 as shown with the arrow. FIG. 20I shows a rotation direction of the thumbwheel 2035 to retract the electrode wire 2010 in the direction shown by the arrow in FIG. 20H. FIG. 20I also shows a pulling or compression direction of the trigger 2030 to maintain the hook 2015 in the extended state while the electrode wire 2010 is retracted into the cannula 2005. Once the electrode wire 2010 is retracted into the cannula 2005, the trigger 2030 may be released so that the hook 2015 may be retracted into the cannula 2005, as shown by the arrow in FIG. 20J. FIG. 20K shows release of the trigger 2030, as well as the flag 2045 displayed in the indicator window 2040 on the handle portion 2020, to confirm that the electrode wire 2010 is retracted. According to this embodiment, a single electrode wire 2010 (that is, a wire that is not looped) may be cinched or held in place by a hook 2015, both the hook 2015 and the electrode wire 2010 may retracted into the cannula 2005 before removal of the cannula 2005, and the likelihood of a protruding tail of the electrode wire 2010 may be reduced.

FIGS. 21A-21C are schematic end views of a cannula 2105 with a looped electrode wire 2110 and a ground wire 2115 arranged therein, with each figure depicting a variation of an arrangement of a hook 2120, 2125, and 2130. In each embodiment, the hook 2120, 2125, 2130 has slots 2135 for receiving a free end of the electrode wire 2110 (or the looped end of the electrode wire 2110), to facilitate retention of the electrode wire 2110. FIG. 21A shows a loop inner arrangement of the hook 2120, in which the slots 2135 are on an inner side relative to a T-divider 2140 of an insert 2145, so that the hook 2120 retains the looped electrode wire 2110 on an inner side thereof. FIG. 21B shows a loop outer arrangement of the hook 2125, in which the slots 2135 of the hook 2125 are on an outer side relative to the T-divider 2140 of the insert 2145, so that the hook 2125 retains the looped electrode wire 2110 on an outer side thereof. And FIG. 21C shows an angled loop arrangement of the hook 2130, in which the slots 2135 of the hook 2130 are arranged at an angle relative to the T-divider 2140, so that the hook 2130 retains the electrode wire 2110 at an angle. The embodiments shown in FIGS. 21A-21C allow for varying degrees of contact with the electrode wire 2110 and the desired tissue 235 and may improve stimulation delivery over a range of tissue diameters. The variations shown in FIGS. 21A-21C also provide for differences in tightness of the loop around the specified tissue 235, providing optimal conditions based on user expectations. The various hook embodiments of FIGS. 21A-21C may be used interchangeably with any of the embodiments described above in which a hook may be included in the electrode apparatus. For example, the embodiments of FIGS. 21A-21C may be used in conjunction with the embodiments of FIG. 18A-18H, 19A-19I, or 20A-20K.

FIGS. 22A-22C are schematic cross-sectional views of a distal end of the cannula 2105 shown in FIG. 21A, with varying positions of the T-divider 2140, and the elements contained therein, including the hook 2120, the looped electrode wire 2110, and the ground wire 2115, relative to a tissue 235. In particular, FIG. 22A shows the T-divider 2140 in a side position, with the electrode wire 2110 extending through the insert 2145 and outward from the distal end of the cannula 2105, and the hook 2120 being near or adjacent to the tissue 235, and the ground wire 2115 being relatively far from the tissue 235. FIG. 22B shows the T-divider 2140 in a bottom position, with the electrode wire 2110 extending through the insert 2145 and outward from the distal end of the cannula 2105, and the ground wire 2115 extending through the insert 2145 to the distal end of the cannula 2105, with both wires being near or adjacent to the tissue 235, and the hook 2120 being far from the tissue 235. And FIG. 22C shows the T-divider 2140 in an upper position, with the electrode wire 2110 extending through the insert 2145 and outward from the distal end of the cannula 2105, and the ground wire 2115 extending through the insert 2145 to the distal end of the cannula 2105, being relatively far from the tissue 235, and the hook 2120 being near or adjacent to the tissue 235. Using FIG. 22A as the starting point, cannula 2105 may be rotated either clockwise to the position shown in FIG. 22B, or counterclockwise to the position shown in FIG. 22C. The embodiments shown in FIGS. 22A-22C allow for varying degrees of contact with the electrode wire 2110 and the desired tissue 235 and may improve stimulation delivery over a range of tissue diameters. The variations shown in FIGS. 22A-22C also provide for differences in tightness of the loop around the specified tissue 235, providing optimal conditions based on user expectations.

Figures 23A, 23B, 23C, 23D, 23E, 24A, 24B, 25A, 25B:
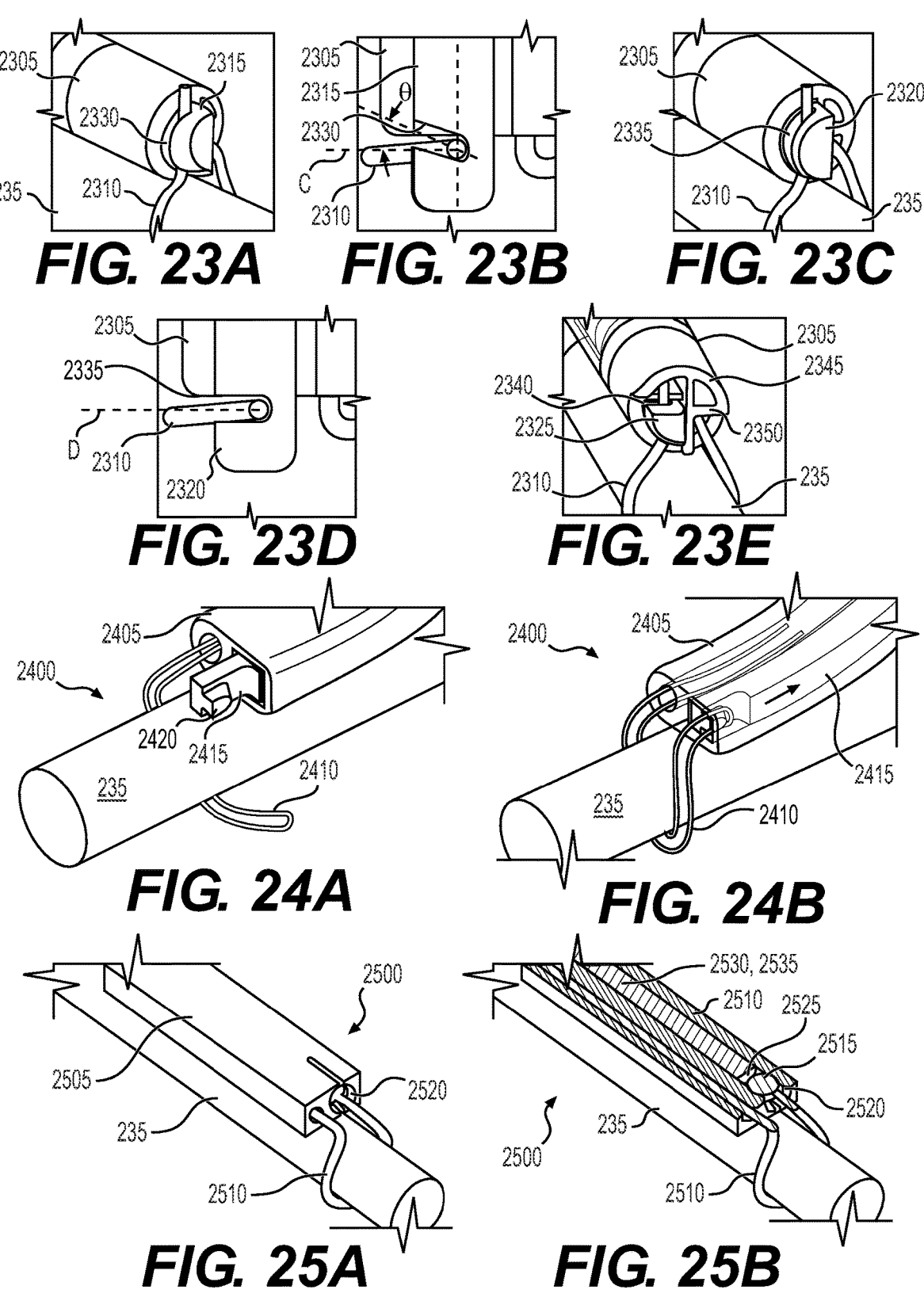
FIGS. 23A-23E are schematic views of a cannula with a hook and an electrode wire arranged therein, according to one or more embodiments.
FIGS. 24A and 24B are schematic views of a distal end of an electrode apparatus, with a looped electrode wire and a hook, according to one or more embodiments.
FIGS. 25A and 25B are schematic views of a distal end of an electrode apparatus, with a ball or ferrule-tipped electrode wire, according to one or more embodiments.

FIGS. 23A-23E are schematic views of a cannula 2305 with a single (or non-looped) electrode wire 2310 and a hook 2315, 2320, 2325 arranged therein. FIGS. 23A-23E depict different sample arrangements of the hook and slot that may be used to securely—but releasably—keep electrode wire 2310 hooked in place when wrapped around tissue 235 during electrical stimulation therapy. FIG. 23A shows a perspective view of a hook 2315 with an angled slot 2330, and FIG. 23B shows a cross-sectional view of the hook 2315 with the angled slot 2330. In this embodiment, once electrode wire 2310 is wrapped around tissue 235, a free end of the electrode wire 2310 is retained within the slot 2330 provided on the hook 2315. The slot 2330 is angled relative to a radial axis C of the hook 2315, for example, at an angle θ, as shown in FIG. 23B. The angle θ may be, for example, in a range of about 0° to about 45°.

FIG. 23C shows a perspective view of a hook 2320 with a straight slot 2335, and FIG. 23D shows a cross-sectional view of the hook 2320 with the straight slot 2335. In this embodiment, once electrode wire 2310 is wrapped around tissue 235, a free end of the electrode wire 2310 is retained within the slot 2335 provided on the hook 2320, and the slot 2335 is collinear with a radial axis D of the hook 2320. FIG. 23E shows a perspective view of a hook 2325 with a recessed slot 2340. In this embodiment, the hook 2325 may be relatively shorter than the hooks 2315, 2320 of the embodiments shown in FIGS. 23A-23D, and the insert 2345 has a '+'-shaped divider 2350, dividing the distal end of the cannula 2305 into quadrants, with the hook 2325 extending through one quadrant. The hook 2325 may retract into the insert 2345, within the cannula 2305, so that it is recessed within the cannula 2305. The hooks 2315 and 2320 of the embodiments shown in FIGS. 23A-23D may also be recessed, or shrouded, within the cannula 2305. Alternatively, the hooks 2315, 2320, and 2325 of the embodiments shown in FIGS. 23A-23E may not be partially recessed, or shrouded, and may extend distally of the distal end of cannula 2305. In each of the embodiments, the arrangement of the slot 2330, 2335, 2340 on the hook 2315, 2320, 2325, respectively, serves to securely retain the electrode wire 2310, while preventing the electrode wire 2310 from protruding into tissue 235 (e.g., a nerve).

The various hook embodiments of FIGS. 23A-23E may be used interchangeably with any of the embodiments described above in which a hook may be included in the electrode apparatus. For example, the embodiments of FIGS. 23A-23E may be used in conjunction with the embodiments of FIG. 18A-18H, 19A-19I, or 20A-20K.

In each of the embodiments shown in FIGS. 21A-23E, the cannula of the electrode apparatus may have an indicia, such as a marker, label, or engraving to indicate to a user the type of hook and cannula design. For example, the indicia may include descriptions including such as "SINGLE SHORT," indicating a short hook embodiment with a single electrode wire, "SINGLE TALL ANGLED," indicating a tall angled hook embodiment with a single electrode wire, "SINGLE TALL STRAIGHT," indicating a tall straight hook embodiment with a single electrode wire, "LOOP OUTER," indicating a looped electrode wire with a slot of the hook being on an outer side thereof, "LOOP INNER," indicating a looped electrode wire with a slot of the hook being on an inner side thereof, and "LOOP ANGLED," indicating a looped electrode wire with a slot of the hook being angled. Any other suitable indicia may be used, including shapes, symbols, colors, and/or numbers, for example.

In each of the embodiments in which the hook has a slot, a surgeon may wrap a free end of the electrode wire around tissue, and insert or nest the free end of the electrode wire into the slot, and then the hook may be retracted at least partially into the cannula to secure the electrode wire in the slot. This may provide a secure connection between the electrode wire and the hook, and a secure connection between the electrode wire and the tissue. Then, by extending the hook distally, the electrode wire may be released from the slot and retracted by pulling the electrode wire in a proximal direction.

FIGS. 24A and 24B are schematic views of a distal end of an electrode apparatus 2400 according to another embodiment. The electrode apparatus 2400 has a cannula 2405, an electrode wire 2410, and a hook 2415 having a projection 2420 extending radially out from a longitudinal axis of hook 2415. The electrode apparatus 2400 may include other features not shown in FIGS. 24A and 24B, including, for example, a ground wire, a handle portion, etc. In this embodiment, the hook 2415 extends through a distal end of the cannula 2405 when in an extended state, and retracts into the distal end of the cannula 2405 when in a retracted state. The extension and retraction of the hook 2415 may be controlled, for example, by the pusher rod 185 described above with respect to the embodiment shown in FIGS. 1-3 and a handle portion with a trigger as described in embodiments above. The electrode wire 2410 extends through a lumen of the cannula 2405, and extends through the distal end of the cannula 2405, as shown in FIGS. 24A and 24B. The electrode wire 2410 is in a looped configuration, so that the electrode wire 2410 may be looped onto the hook 2415, as shown in FIG. 24B.

The looped electrode wire 2410 may extend from a distal end of cannula 2405, be wrapped around a tissue 235, and then placed onto the hook 2415 (e.g., using a tool such as a forceps) and may catch on the projection portion of the hook 2415. The hook 2415 may then be retracted into the cannula 2405, as shown in FIG. 24B. When the hook 2415 retracts into the cannula 2405, the electrode wire 2410 may be securely retained by the hook 2415. In addition, once retained by the hook 2415, the electrode wire 2410 may be tightened or tensioned to ensure sufficient contact between the electrode wire 2410 and the tissue 235. The electrode wire 2410 may be tensioned using, for example, the slide mechanism described above with respect to the embodiment shown in FIGS. 1-3, or a thumbwheel, as described in FIGS. 18A-18H, 19A-19I, and 20A-20K, or any other suitable actuator. To release the wire 2410, the hook 2415 may be extended outward from the distal end of the cannula 2405, and the electrode wire 2410 may be removed from the hook 2415 by, for example, loosening of the electrode wire 2410 via the slide mechanism or thumbwheel. Once the electrode wire 2410 is released, the hook 2415 and the electrode wire 2410 may be retracted into the cannula 2405 for removal of cannula 2405 from a surgical site. In other embodiments, one or both of hook 2415 and electrode wire 2410 may remain in an extended state during removal. By virtue of the embodiment shown in FIGS. 24A and 24B, the electrode wire 2410 may be easily released when the hook 2415 is in an extended state. In addition, the use of a stranded wire in this embodiment may prevent excessive force on the tissue 235. In particular, a stranded wire may be more flexible and may have more "give" in it. A stranded wire may be more likely to release due to pressure placed on it by the tissue 235, whereas a solid wire may be more likely to retain its shape.

FIGS. 25A and 25B are schematic views of a distal end of an electrode apparatus 2500 according to another embodiment. The electrode apparatus 2500 includes a cannula 2505, and an electrode wire 2510 with a ball or ferrule 2515 at an end thereof. FIG. 25A shows the cannula 2505 with the electrode wire 2510 extending distally from a distal end, wrapping around a tissue 235, and reentering the cannula 2505 via an opening 2520. FIG. 25B shows a cut-away schematic view of the distal end of the electrode apparatus 2500, showing the ball 2515 of the electrode wire 2510 located within a cavity 2525 of the cannula 2505. The cavity 2525 may be correspondingly shaped like the ball 2515 or may have any other suitable shape. The opening 2520 may be narrower than the cavity 2525 and slightly narrower than a diameter of the ball 2515, in order to retain the ball 2515 of the electrode wire 2515 within the cavity 2525 of the cannula 2505. The material that forms the cannula 2505 may have some flexibility to allow for deflection of the relatively narrower opening 2520 and insertion of the ball 2515 into the cavity 2525, while also having sufficient strength to retain the ball 2515 within the cavity 2525. A release mechanism 2530 may also be provided in the cannula 2405, and includes a rod 2535 extending through the cannula 2505 to the cavity 2525, as shown in FIG. 25B. Upon actuation of the release mechanism 2530, the rod 2535 moves in a distal direction and pushes the ball 2515 outward from the cavity 2525, for release of the electrode wire 2510. Then, the electrode wire 2510 unwraps from the tissue 235, and may be retracted into the cannula 2505 and removed from a surgical site.

One benefit of the embodiment shown in FIGS. 25A and 25B is that the apparatus 2500 may be simple to assemble and thus may reduce manufacturing costs. In addition, feedback confirming removal of the ball 2515 from the cannula 2505 may be received due to the force of the detent of the ball 2515 being pushed out of the cannula 2515 by the rod 2535. Further, release of the ball 2515 may be confirmed by a depth to which the rod 2535 of the release mechanism 2530 extends to push the ball 2515 in a distal direction.

FIGS. 26A and 26B are schematic views of a distal end of an electrode apparatus 2600 according to another embodiment. The electrode apparatus 2600 has a cannula 2605, an electrode wire 2610, and a spool mechanism 2615. In particular, FIG. 26A shows the electrode apparatus 2600 with a coiled wire 2610 extending from the spool mechanism 2615 at the distal end of the cannula 2605. FIG. 26B shows a cut-away schematic view of the electrode apparatus 2600, showing a spool portion 2620 of the spool mechanism 2615. The electrode wire 2610 is wound around the spool portion 2620, such that rotation of the spool mechanism 2615 causes rotation and translation, relative to a longitudinal axis of the cannula 2605, of the electrode wire 2610. By this configuration, rotating the spool portion 2620, e.g., in a direction of the arrow E, rotates the coiled electrode wire 2610 and causes the coiled electrode wire 2610 to translate in a distal direction, and rotating the spool portion 2620 in an opposite direction rotates the coiled electrode wire 2610 and causes the coiled electrode wire 2610 to translate in a proximal direction. Thus, the coiled electrode wire 2610 can be rotated to extend distally of the distal end of the cannula 2605 during a surgical procedure, to thereby be wrapped around a tissue 235, and can be rotated in an opposite direction to withdraw or retract proximally into the cannula 2605, for removal of the electrode apparatus 2600 from a surgical site. Rotation of the spool portion 2620 may be controlled, for example, by a knob located within the handle portion, such as the knob 825 of the embodiment shown in FIGS. 9A-9F, or with a thumbwheel or slide mechanism as described above, or another suitable actuator. The actuator may be mechanically coupled to the spool portion 2620. By virtue of this embodiment, an electrode apparatus 2600 is provided in which an electrode wire 2610 may not press into a tissue 235 during implantation or extraction of the electrode apparatus 2600.

FIGS. 27A and 27B are schematic views of a distal end of an electrode apparatus 2700 according to another embodiment. The electrode apparatus 2700 includes a cannula 2705, an electrode wire 2710, and an electrode wire sleeve 2715, with a free end of the electrode wire 2710 being coiled and extending from the distal end of the sleeve 2715. In particular, FIG. 27A shows a distal end of the cannula 2705, alongside a tissue 235, with the electrode wire 2710 extending beyond the distal end of the cannula 2705 and wrapped around the tissue 235. The electrode wire 2710 extends through the sleeve 2715, and a distal end of the electrode wire 2710 is coiled. FIG. 27B shows a schematic view of the electrode apparatus 2600, with the cannula 2705 and the sleeve 2715 shown in hidden lines. The electrode wire 2710 extends from a proximal end of the cannula 2705, through a channel within the sleeve 2715, and extends distally outward from the distal end of the sleeve 2715. In this embodiment, only a distal-most portion of the electrode wire 2710 is in a coiled configuration, which may be done by a surgeon wrapping the electrode wire 2710 around a tissue 235 during a surgical procedure. The electrode wire 2710 may be pulled into the channel of the sleeve 2715 for removal of the electrode apparatus 2700. The electrode wire 2710 may be relatively flexible so that, as the electrode wire 2710 is pulled into the channel, the electrode wire 2710 uncoils and straightens. By virtue of this embodiment, an electrode apparatus 2700 is provided in which the electrode wire 2710 may unravel relative to the tissue 235, without pressing into the tissue 235, to be easily and safely removed following electrical stimulation therapy.

FIG. 28 is a schematic view of a pre-coiled electrode wire 2810 of an electrode apparatus according to one of the embodiments described above. The pre-coiled electrode wire 2810 of this embodiment may be used, for example, in an electrode apparatus according to the embodiment shown in FIGS. 8A-9F or any other suitable embodiment. In particular, a portion of the electrode wire 2810 that extends beyond a distal end of a cannula 2805 may be wound into a coil shape, prior to placement around an end of a tissue 235, rather than being wound around a tissue 235 during a surgical procedure. This embodiment allows for an electrode wire 2810 formed of a material having a relatively high tensile strength. Further, the higher strength of pre-coiled electrode wire 2810 may make it less susceptible to spring back, which may occur when the electrode wire 2810 is bent into a particular configuration using a tool or a user's hand and, upon release of the pre-coiled electrode wire 2810, the wire may revert slightly from the configuration (e.g., when the electrode wire 2810 is coiled and, upon release, the coil formed by the electrode wire 2810 expands or loosens). Another potential benefit of this embodiment may be that a kit comprising an electrode apparatus may also include multiple pre-coiled electrode wires 2810 having a range of coil diameters, allowing the electrode apparatus to be used on a tissues of varying sizes. In other aspects, pre-coiled electrode wires 2810 may be sold separately.

FIG. 29 is a schematic view of an x-looped wire 2910 which may be used in conjunction with any of the embodiments described above. The x-looped electrode wire 2910 of this embodiment may be used, for example, in an electrode apparatus according to the embodiment shown in FIGS. 1-3, 18A-18H, and 19A-19I. As shown, the looped electrode wire 2910 extends from a distal end of a cannula 2905, winds around a tissue 235, and reenters the cannula 2905 after crossing, or forming an X with, the portion of the electrode wire 2910 just distal to the distal end of the cannula 2905. By virtue of this embodiment, contact between the electrode wire 2910 and majority of the periphery or an entire periphery of the tissue 235 may be achieved.

In each of the embodiments of an electrode apparatus described herein, the electrode wire, as well as any other end effectors, is retractable within the cannula, and may be retracted during insertion of the cannula in a surgical site and/or removal of the cannula from a surgical site. In addition, although directions of rotation of a thumbwheel, sliding of a slider, and compression or release of a trigger are specified in the embodiments described above, the directions may vary from those described and shown. In particular, the directions of rotation of the thumbwheel, sliding of the slider, and compression or release of the trigger may be opposite to those described and shown above, in order to extend and retract the respective elements (i.e., a hook or an electrode wire). For example, a trigger mechanism, provided on the handle and operably coupled to the hook, may be configured to move the hook in one of a distal direction and a proximal direction, upon compression of a trigger of the trigger mechanism, and to move the hook in the other one of the distal direction and the proximal direction, upon release of the trigger. As another example, a slide mechanism, provided on the handle and operably coupled to the electrode wire, may be configured to move the electrode wire in one of a distal direction and a proximal direction, upon translation of a slide to a distal position within a slot, and to move the electrode wire in the other one of the distal direction and the proximal direction, upon translation of the slide to a proximal position within the slot. As still another example, a thumbwheel, provided on the handle and operably coupled to the electrode wire, may be configured to move the electrode wire in one of a distal direction and a proximal direction, upon rotation of the thumbwheel in a distal direction, and to move the electrode wire in the other one of the distal direction and the proximal direction, upon rotation of the thumbwheel in a proximal direction.

As noted above with respect to the various embodiments of the electrode apparatus, the surgical site may be closed with a small opening remaining through which the cannula passes while electrical stimulation therapy continues. Upon completion of electrical stimulation therapy, the electrode wire may be disengaged from the tissue, and the electrode wire the cannula and the electrode wire may be retracted or withdrawn through the small opening. The small opening may then be closed without requiring further surgical procedures, without requiring use of an operation room, and without requiring further involvement of a surgeon, thus reducing the overall cost and complexity of procedures including electrical stimulation therapy.

The electrode apparatus of the embodiments described herein may be disposable or reusable. In this regard, exemplary electrode apparatuses may include relatively simple mechanical connections and components, to reduce the cost of manufacturing the apparatuses.

FIG. 30 shows a flowchart of a method 3000 of providing electrical stimulation to a tissue using an electrode apparatus according to one or more embodiments. For example, the method 3000 shown in FIG. 30 may use an electrode apparatus according to the embodiment shown in one of FIGS. 18A-24B and 29. The method 3000 includes a step 3005 of placing a distal portion of a cannula in a surgical site, adjacent to the tissue. The distal portion of the cannula may be placed by a surgeon, for example. In some aspects, once the cannula is placed at the surgical site, a more proximal portion of the cannula may be secured to the patient, as described above and shown, e.g., in FIGS. 4A-7F.

Once placed at the surgical site, one or both of an electrode wire or a hook may be extended from the distal end of the cannula. The electrode wire may be a looped wire or a single wire. The method 3000 further includes a step 3010 of wrapping a distal end of the electrode wire around a periphery of the tissue. The distal end of the electrode wire may be wrapped using a tool, such as a forceps. The method 3000 also includes a step 3015 of engaging the distal end of the wrapped electrode wire with a hook of the electrode apparatus extending from a distal end of the cannula. This step may also be performed by a surgeon using a tool. Then, the method 3000 includes a step 3020 of retracting the hook, with the distal end of the electrode wire secured by the hook, into the distal end of the cannula. This step allows that the distal end of the electrode wire to be securely held in place by the hook within the cannula to promote contact with the tissue.

Next, a step 3025 may be performed, in which electricity is supplied from an electrical supply, such as an electrical stimulation platform as described herein. This step is performed for a predetermined period of time. For example, the period of time may be in a range of about 1 minute to about 1 month, and, in particular applications, about 1 minute to about 60 minutes, or in other applications, about 1 hour to about 3 weeks, for example. During this period of time, the surgical site may be substantially closed, for example, using sutures, while a small opening in the skin of the patient remains through which the cannula remains inserted in the patient. Then, when the period of time has elapsed and supply of electricity has stopped, in a step 3030, the hook is extended out of the distal end of the cannula, allowing the distal end of the electrode wire to disengage from the hook. Finally, the method 3000 includes a step 3035 of removing the electrode wire from the tissue, and retracting the cannula from the surgical site. In some aspects, one or both of the electrode wire or the hook may be retracted into the cannula prior to retracting the cannula from the surgical site. Steps 3025-3035 may be performed by a surgeon or another medical professional, such as a nurse, after the patient has been moved out of an operating room. The small opening may then be closed.

Although the method 3000 is described as including steps 3005 to 3035, the method may include a subset of these step or additional steps.

Figure 31:
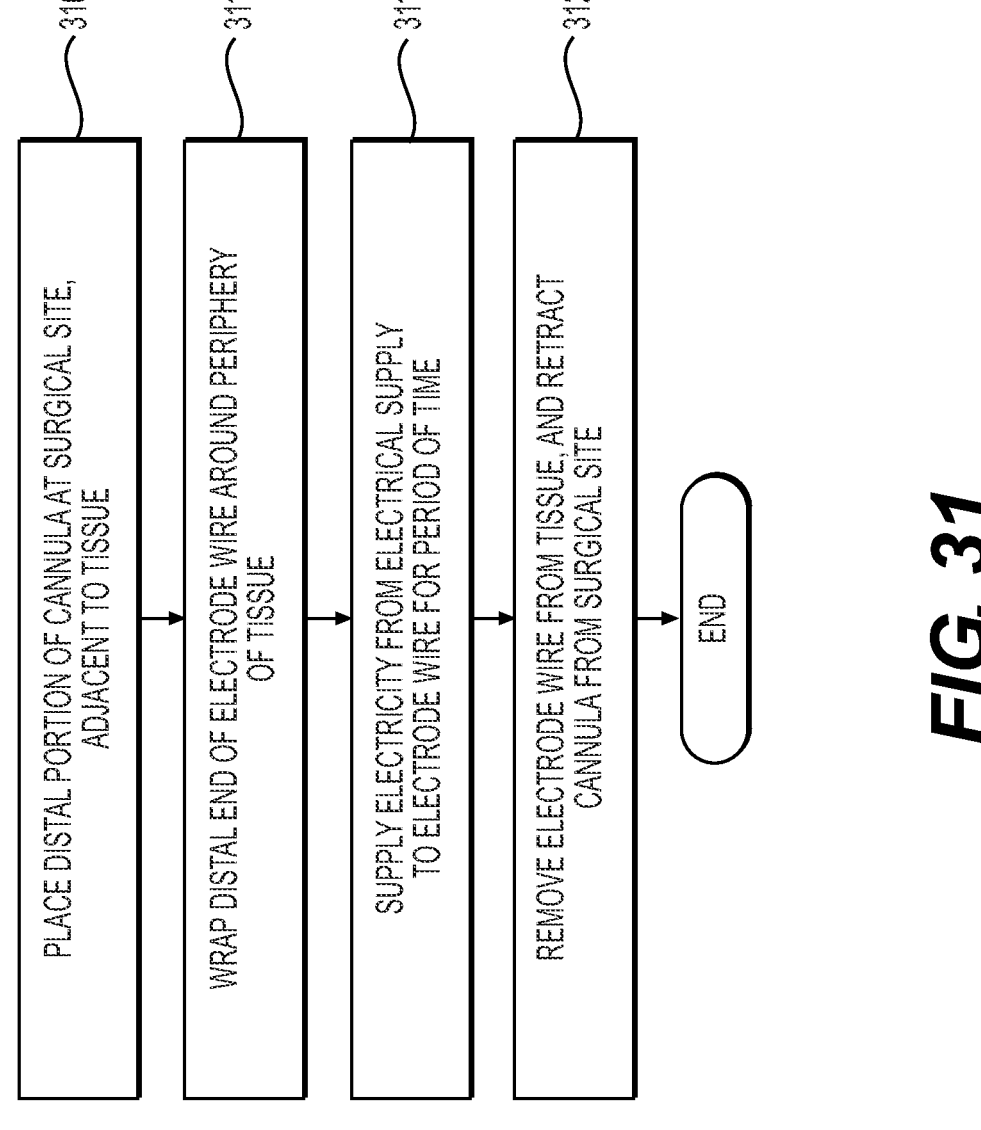
FIG. 31 depicts a flowchart of another method of providing electrical stimulation to a tissue using an electrode apparatus, according to one or more embodiments.

FIG. 31 shows a flowchart of another method 3100 of providing electrical stimulation to a tissue using an electrode apparatus according to any of the embodiments described above. For example, the method 3100 shown in FIG. 31 may use an electrode apparatus according to the embodiment shown in one of FIGS. 8A-9F and 26A-28. The method 3100 includes a step 3105 of placing a distal portion of a cannula in a surgical site, adjacent to the tissue. The distal portion of the cannula may be placed by a surgeon. In some aspects, once the cannula is placed at the surgical site, a more proximal portion of the cannula may be secured to the patient, as described above and shown, e.g., in FIGS. 4A-7F.

Once placed at the surgical site, one or both of an electrode wire or a hook may be extended from the distal end of the cannula. The electrode wire may be a looped or a single wire. The method 3100 further includes a step 3110 of wrapping a distal end of the electrode wire around a periphery of the tissue. The distal end of the electrode wire may be wrapped using a tool, such as a forceps. In an alternative embodiment, a distal portion of the electrode wire may be pre-formed in a coil, or pre-coiled, and this step may include rotating the electrode apparatus and/or the electrode wire so that the coiled portion of the electrode wire wraps around a periphery of the tissue. The method 3100 also includes a step 3115 of supplying electricity from an electrical supply, such as an electrical stimulation platform as described herein. This step is performed for a predetermined period of time. For example, the period of time may be in a range of about 1 minute to about 60 minutes, for example. During this period of time, the surgical site may be substantially closed, for example, using sutures, while a small opening in the skin of the patient remains through which the cannula remains inserted in the patient. Then, when the period of time has elapsed and supply of electricity has stopped, in a step 3120, the electrode wire is detached from the tissue and retracted into the distal end of the cannula, and the cannula is retracted from the surgical site out of the small opening in the skin. Steps 3115 and 3120 may be performed by a surgeon or another medical professional, such as a nurse, after the patient has been moved out of an operating room. The small opening may then be closed.

Although the method 3100 is described as including steps 3105 to 3120, the method may include a subset of these step or additional steps.

The embodiments of the electrode apparatus and the related methods described herein may permit relatively longer durations of electrical stimulation therapy without requiring longer operative times or additional procedures to remove the electrodes from the patient following therapy. In addition, an electrode apparatus according to the embodiments described herein may allow a patient to be moved out of an operation room upon completion of the surgical procedure into a recovery space, where electrical stimulation therapy may continue. Further, the electrode apparatus may be safely and easily removed from the patient upon completion of the electrical stimulation therapy, without requiring further surgical techniques, requiring an operating room and/or a surgeon. Although the electrode apparatus is described as being used for electrical stimulation therapy, the apparatus may have other uses, including but not limited to, pain management and diagnostic applications. Further, due to the relatively low current passing through the electrode wire into the tissue and the ground wire being located close to the electrode wire, the electrode apparatus according to the embodiments described herein has a relatively small zone of impact, with little impact on tissue surrounding the tissue subject to electrical stimulation.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An electrode apparatus, comprising:
   a handle;
   a cannula extending from a distal end of the handle, wherein the cannula includes at least one lumen therein;

a ground wire extending through the cannula;

an electrode wire extending through the handle, and through the cannula, the electrode wire being extendable and retractable relative to a distal end of the cannula;

a pusher rod extending from the handle, through the cannula, alongside the electrode wire; and a hook provided on a distal end of the pusher rod, the hook being extendable and retractable relative to the cannula.

2. The electrode apparatus of claim 1, wherein a distal end of the electrode wire is in a looped configuration.

3. The electrode apparatus of claim 1, wherein the electrode wire is a single, un-looped, electrode wire.

4. The electrode apparatus of claim 1, further comprising a trigger mechanism, provided on the handle and operably coupled to the hook via the pusher rod, and being configured to move the hook in one of a distal direction and a proximal direction, upon compression of a trigger of the trigger mechanism, and to move the hook in the other one of the distal direction and the proximal direction, upon release of the trigger.

5. The electrode apparatus of claim 1, further comprising a slide mechanism, provided on the handle and operably coupled to the electrode wire, and being configured to move the electrode wire in one of a distal direction and a proximal direction, upon translation of a slide to a distal position within a slot, and to move the electrode wire in the other one of the distal direction and the proximal direction, upon translation of the slide to a proximal position within the slot.

6. The electrode apparatus of claim 1, further comprising a thumbwheel, provided on the handle and operably coupled to the electrode wire, and being configured to move the electrode wire in one of a distal direction and a proximal direction, upon rotation of the thumbwheel in a distal direction, and to move the electrode wire in the other one of the distal direction and the proximal direction, upon rotation of the thumbwheel in a proximal direction.

7. The electrode apparatus of claim 6, further comprising an indicator window, provided on the handle, and configured to display a flag when the electrode wire is retracted into the distal end of the cannula.

8. The electrode apparatus of claim 1, wherein the electrode wire is formed of a biocompatible material.

9. The electrode apparatus of claim 8, wherein the biocompatible material is selected from the group consisting of: Nitinol®, copper, annealed copper, gold plated copper, and gold plated wire.

10. The electrode apparatus of claim 1, wherein the electrode wire is formed of stranded wire.

11. The electrode apparatus of claim 5, further comprising an indicator window, provided on the handle, and configured to display a flag when the electrode wire is retracted into the distal end of the cannula.

12. The electrode apparatus of claim 1, wherein a distal end of the hook is rounded.

13. The electrode apparatus of claim 1, wherein the hook has a protrusion on one surface thereof for grasping a distal end of the electrode wire.

14. The electrode apparatus of claim 1, further comprising an insert provided within a distal end of the cannula, the insert having a T-shaped divider at a distal end thereof forming a plurality of openings through which the ground wire, the electrode wire, and the hook are configured to extend.

15. The electrode apparatus of claim 14, wherein the insert further as a circumferential slot, and the ground wire is configured to be inserted into the circumferential slot.

16. The electrode apparatus of claim 1, wherein one or more proximal portions of the electrode wire are insulated, and a distal portion of the electrode wire is not insulated.

17. The electrode apparatus of claim 1, wherein the electrode wire has a welded tip without insulation, and a distal end of the electrode wire is located distally of the hook.

* * * * *